United States Patent [19]
Cover et al.

[11] Patent Number: 5,859,219
[45] Date of Patent: Jan. 12, 1999

[54] **PURIFIED VACUOLATING TOXIN FROM *HELICOBACTER PYLORI* AND METHODS TO USE SAME**

[75] Inventors: Timothy L. Cover; Martin J. Blaser, both of Nashville, Tenn.

[73] Assignee: Vanderbilt University, Nashville, Tenn.

[21] Appl. No.: 295,643

[22] PCT Filed: Feb. 24, 1993

[86] PCT No.: PCT/US93/01558

§ 371 Date: Oct. 27, 1994

§ 102(e) Date: Oct. 27, 1994

[87] PCT Pub. No.: WO93/16723

PCT Pub. Date: Sep. 2, 1993

Related U.S. Application Data

[63] Continuation-in-part of Ser. No. 841,644, Feb. 26, 1992.

[51] Int. Cl.$^6$ .................. A61K 39/106; C12N 15/31; C12N 1/20; C07H 21/04
[52] U.S. Cl. .................. 536/22.1; 536/23.7; 536/24.3; 536/24.32; 435/252.3; 435/320.1; 435/69.1; 435/69.3; 435/91.1; 424/236.1
[58] Field of Search .................. 435/69.3, 91, 172.1, 435/252.1, 320, 7.1, 6; 424/184.1, 185.1; 536/22.1, 23.7, 24.3, 24.32

[56] References Cited

U.S. PATENT DOCUMENTS

| | | |
|---|---|---|
| 4,683,202 | 7/1987 | Mullis . |
| 4,882,271 | 11/1989 | Evans et al. .................. 435/7 |

FOREIGN PATENT DOCUMENTS

| | | | |
|---|---|---|---|
| WO93/16723 | of 0000 | WIPO | .................. A61K 39/100 |
| WO 94/04161 | 3/1994 | WIPO | .................. A61K 31/71 |

OTHER PUBLICATIONS

Crabtree et al. "Mucosal IgA recobnition of *Helicobacter pylori* . . . " *Lancet* 338:332–335, 1991.
Goosens et al. "In vitro cytotoxin production . . . " *Microb. Ecol. health Dis.* 4:, S130, 1991.
Cover et al. "Effect of Urease on HeLa Cell . . . ", *Infect. and Immun.* 59(4):1264–1270, 1991.
Peterson, Walter L. "*Helicobacter pylori* and Peptic Ulcer Disease", *Current concepts* 324(15):1043–1048, Apr. 1991.
Nomura et al. "*Helicobacter pylori* Infection and Gastric Carcinoma . . . " *N. Engl. J. Med.* 325:1132–1136, 1991.
Parsonnet et al. "*Helicobacter pylori* Infection in Intestinal . . . ", *J. Natl Cancer Inst.* 83(9):640–643, 1991.
Leunk et al. "Antibody to Cytotoxin in Infection . . . " *J. Clin. Microbiol.* 28(6):1181–1184, Jun. 1990.
Blaser, Martin J. "*Helicobacter pylori* and the Pathogenesis . . . ", J. Infect. Dis. 161;626–633, 1990.
Cover et al. "Characterization of and Human Serologic Response . . . " *Infect. and Immun.* 58(3):603–610, Mar. 1990.
Eaton et al. "*Campylobacter pylori* Virulence Factors . . . " *Infect. and Immun.* 57(4):1119–1125, Apr. 1989.
Figura et al. "Cytotoxin Production by *Campylobacter pylori* . . . " *J. Clin. Microbiol.* 27(1):225–226, Jan. 1989.
Leunk et al. "Cytotoxic activity in broth–culture filtrates . . . " *J. Med. Microbiol.* 26:93–99, 1988.
Young et al PNAS 80:1194–1198, 1983.
Foxall et al, Journal of Clinical Microbiology 30:739–741 1992.
Cover et al Infecton & Immunity 58:603–610, 1990.
Leunk et al J Med Microbiology 26:93–99, 1988.
Schmitt et al Molecular Microbiology 12:307–319 1994.
Owen et al Eur Journal of Epidemiology 43:315–321, 1993.
Wyle et al European Journ of Gastroenterology 5K59–515 1993.
Covent et al, Journal of Biol Chem 267:10570–75, 1992.
Suggs et al, PNAS 78:6613–6617, 1981.
Atherton et al, The J. of Biol. Chem 270:1–7 1995.
Telford et al European J. Gastroenterol Hepatol 5/Suppl. 2:522–524, 1993 Abstract Only.
Owen et al FEMS Microbiology Letters 79:199–204 1991.
Umata et al. "The Cytotoxic Action of Diptheria Toxin and Its Degradation in Intact Vero Cells are Inhibited by Balifomycin A1, a Specific Inhibitor of Vacuolar–Type H$^+$–ATPase" *J. Biol. Chem.* 275(35):21940–21945, Dec., 1990.

*Primary Examiner*—Hazel F. Sidberry
*Attorney, Agent, or Firm*—Needle & Rosenberg, PC

[57] ABSTRACT

This invention relates to a purified *Helicobacter pylori* vacuolating toxin and methods to use this toxin to produce protective antibodies against *H. pylori* infection. Antiserum to this antigen can be used to detect the toxin. Methods to detect anti-toxin antibodies determine the susceptibility of a patient to develop peptic ulcer disease, gastric carcinoma, or other clinical consequences of *H. pylori* infection.

7 Claims, 8 Drawing Sheets

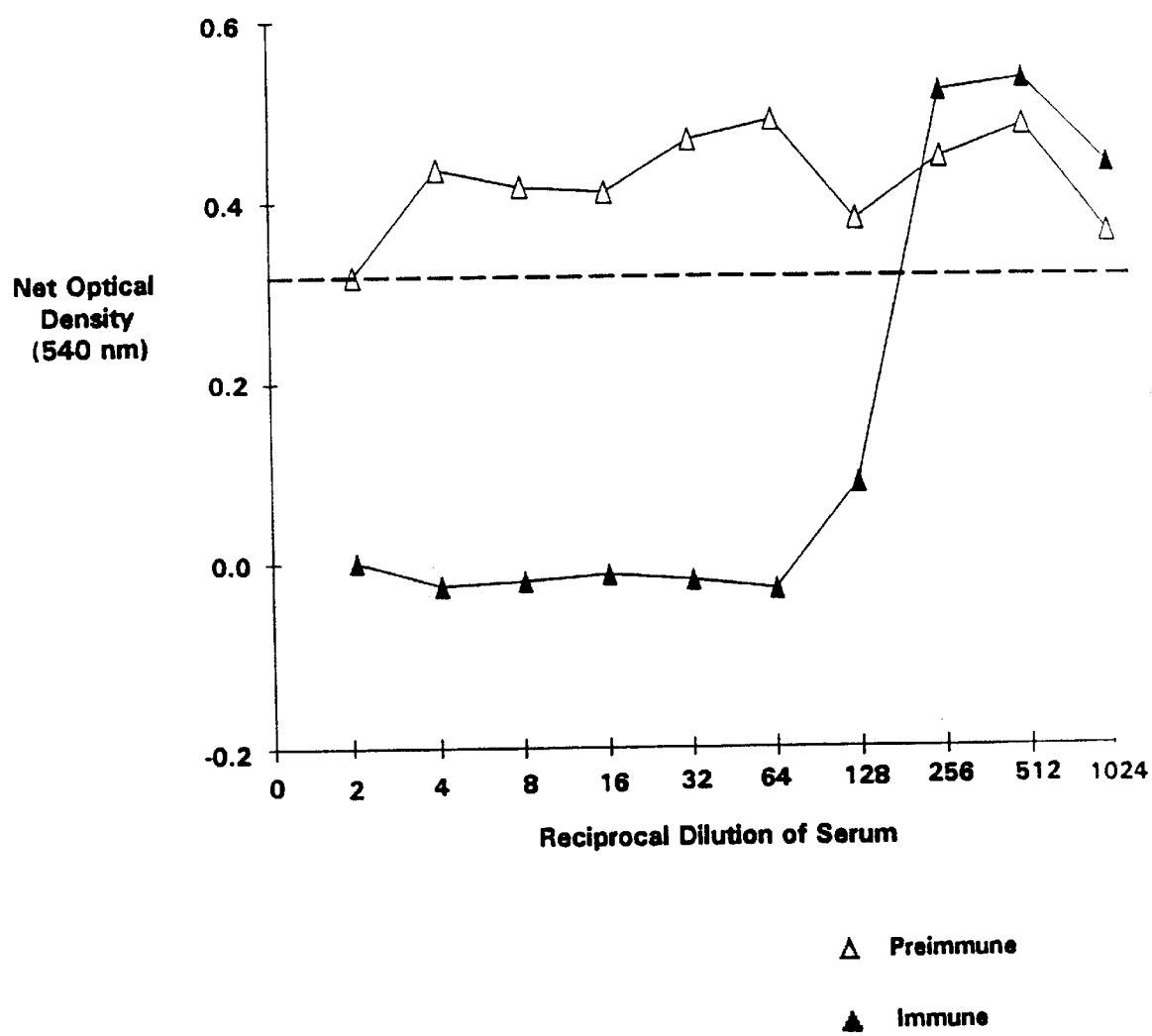

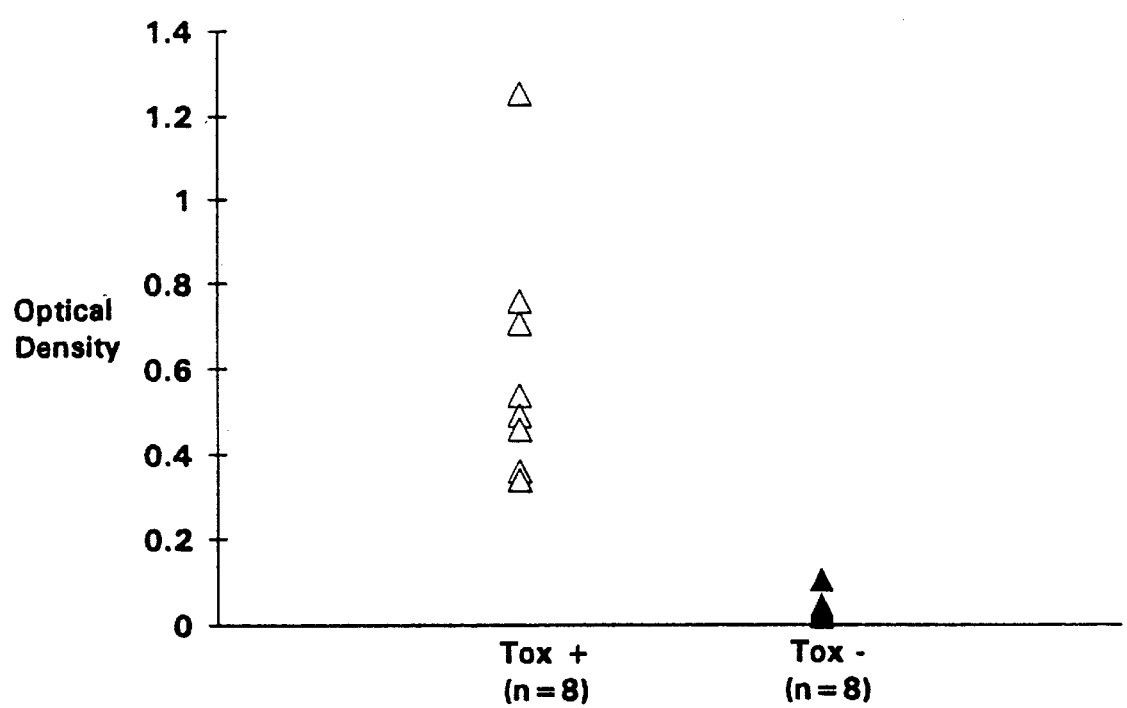

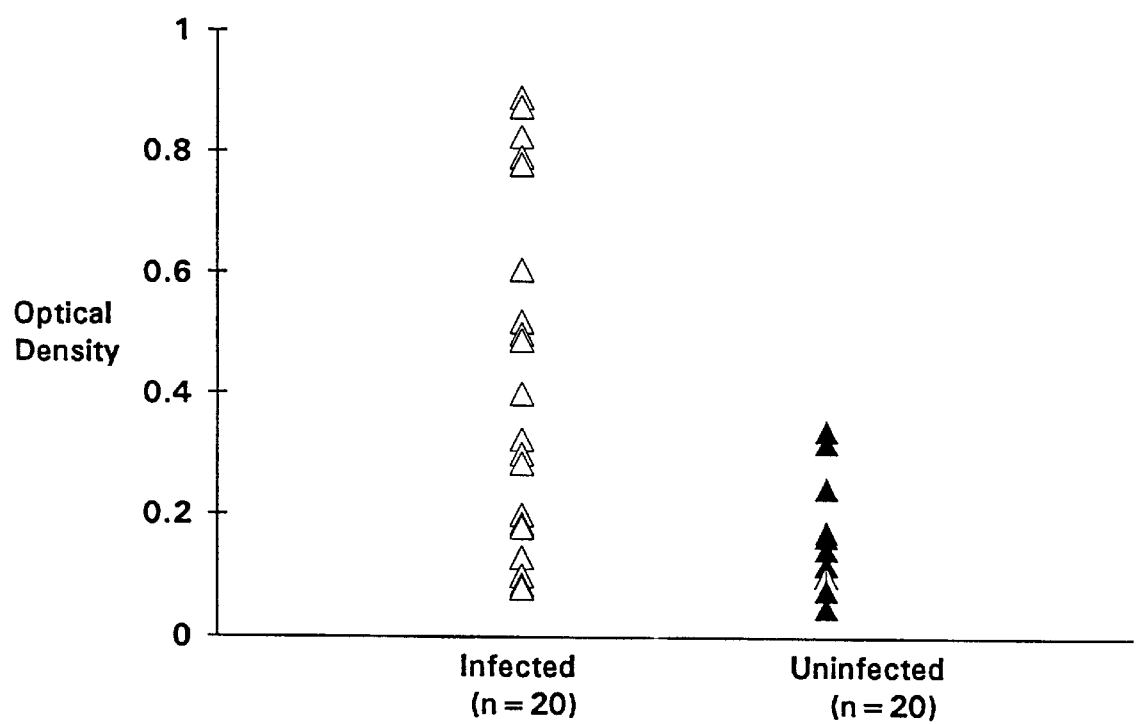

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1412 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
GCCTTTTTTA  CAACCGTGAT  CATTCCAGCC  ATTGTTGGGG  GCATCGCTAC  AGGCACCGCT      60

GTAGGAACGG  TCTCAGGGCT  TCTTGGCTGG  GGGCTCAAAC  AAGCCGAAGA  AGCCAATAAA     120

ACCCCAGATA  AACCCGATAA  AGTTTGGCGC  ATTCAAGCAG  GAAAAGGCTT  TAATGAATTC     180

CCTAACAAGG  AATACGACTT  ATACAAATCC  CTTTTATCCA  GTAAGATTGA  TGGAGGTTGG     240

GATTGGGGA   ATGCCGCTAC  GCATTATTGG  ATCAAAGGCG  GGCAATGGAA  TAAGCTTGAA     300

GTGGATATGA  AAGACGCTGT  AGGGACTTAT  AAACTCTCAG  GGCTAAGGAA  CTTTACTGGT     360

GGGGATTTAG  ATGTCAATAT  GCAAAAAGCC  ACCTTGCGCT  TGGGCCAATT  CAATGGCAAT     420

TCTTTCACAA  GCTATAAGGA  TAGTGCTGAT  CGCACCACAA  GAGTGGATTT  CAACGCTAAA     480
```

| | | | | | |
|---|---|---|---|---|---|
| AATATCTTAA | TTGATAATTT | TTTAGAAATC | AATAATCGTC | TGGGTTCTGG | AGCCGGGAGG | 540
| AAAGCCAGCT | CTACGGTTTT | GACTTTGCAA | GCTTCAGAAG | GGATTACTAG | CAGTAAAAAT | 600
| GCTGAAATTT | CTCTTTATGA | TGGCGCTACG | CTCAATTTGG | CTTCAAACAG | CGTTAAATTA | 660
| AATGGCAATG | TGTGGATGGG | CCGTTTGCAA | TACGTGGGAG | CGTATTTGGC | CCCTTCATAC | 720
| AGCACGATAA | ACACTTCAAA | AGTGACAGGG | GAAGTGAATT | TTAACCATCT | CACTGTGGGC | 780
| GATCACAACG | CCGCTCAAGC | AGGCATTATC | GCTAGTAACA | AGACTCATAT | TGGCACACTG | 840
| GATTTGTGGC | AAAGCGCGGG | GTTAAATATC | ATTGCCCCTC | CCGAAGGTGG | CTACAAGGAT | 900
| AAACCTAATA | ATACCCCTTC | TCAAAGTGGT | GCTAAAAACG | ACAAACAAGA | GAGCAGTCAA | 960
| AATAATAGTA | ACACTCAGGT | CATTAACCCA | CCCAATAGCA | CGCAAAAAAC | AGAAGTTCAA | 1020
| CCCACGCAAG | TCATTGATGG | GCCTTTTGCG | GGTGGCAAAG | ACACGGTTGT | CAATATTGAT | 1080
| CGCATCAACA | CTAAAGCCGA | TGGCACGATT | AAAGTGGGAG | GGTTTAAAGC | TTCTCTTACC | 1140
| ACCAACGCGG | CTCATTTGAA | TATCGGCAAA | GGCGGTGTCA | ATCTGTCCAA | TCAAGCGAGC | 1200
| GGGCGCACCC | TTTTAGTGGA | AAATCTAACC | GGGAATATCA | CCGTTGATGG | GCCTTTAAGA | 1260
| GTGAATAATC | AAGTGGGTGG | CTATGCTTTG | GCAGGATCAA | GCGCGAATTT | TGAATTTAAG | 1320
| GCTGGTGTGG | ATACTAAAAA | CGGCACAGCC | ACTTTCAATA | ACGATATTAG | TCTGGGAAGA | 1380
| TTTGTGAATT | TAAAGGTGGA | TGCTCATACA | GG | | | 1412

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:2:

Ala Phe Phe Thr Thr Val Ile Ile Pro Ala Ile Val Gly Gly Ile Ala
 1              5                   10                   15

Thr Gly Thr Ala Val Gly Thr
            20

( 2 ) INFORMATION FOR SEQ ID NO:3:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

Ala Phe Phe Thr Thr Val Phe Gly Leu Glu Ala Ile Val Lys Ile Val
 1              5                   10                   15

Gly Leu Arg Tyr His Tyr Phe Thr
            20

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

Leu Phe Phe Thr Thr Tyr Ile Ile Ile Ser Phe Leu Ile Val Val Asn
1               5                   10                  15

Met Tyr Ile Ala Ile Ile Leu Glu
            20

( 2 ) INFORMATION FOR SEQ ID NO:5:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:5:

Ala Phe Phe Ser Thr Asn Cys Val Glu Gly Thr Ala Val Gly Ile Val
1               5                   10                  15

Ile Ser Thr Gly Asp Arg Thr
            20

( 2 ) INFORMATION FOR SEQ ID NO:6:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

Val Ala Leu Leu Val Cys Leu Ile Pro Thr Thr Ile Gly Gly Leu Leu
1               5                   10                  15

Ser Ala Ser Ala Val Ala Gly
            20

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

Glu Met Ile Met Lys Ser Ile Ile Pro Val Val Met Ala Gly Ile Ile
1               5                   10                  15

Ala Ile Tyr Gly Leu Val Val
            20

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

Ala Phe Leu Leu Ala Val Ile Ile Gly Val Ser Ala Gly Val Ile Ala

-continued

```
           1               5                      10                     15
       Ala  Leu  Lys  Gln  Asn  Thr  Arg
                          20
```

( 2 ) INFORMATION FOR SEQ ID NO:9:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

```
       Ala  Phe  Phe  Thr  Pro  Phe  Ile  Thr  Ser  Ala  Ile  Asn  Phe  Tyr  Tyr  Gly
        1               5                      10                     15
       Tyr  Val  Phe  Met  Gly  Cys  Leu
                          20
```

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:10:

```
       Phe  Phe  Phe  Ala  Ser  Leu  Met  Ile  Leu  Ser  Ile  Val  Phe  Val  Phe  Phe
        1               5                      10                     15
       Leu  Ile  Pro  Glu  Thr  Lys  Gly
                          20
```

( 2 ) INFORMATION FOR SEQ ID NO:11:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:11:

```
       Gln  Phe  Leu  Ala  Ser  Val  Gln  Thr  Met  Glu  Ile  Val  Pro  Ser  Phe  Ala
        1               5                      10                     15
       Val  Gly  Ser  Ala  Val  Gly  Leu
                          20
```

( 2 ) INFORMATION FOR SEQ ID NO:12:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:12:

```
       Ala  Phe  Phe  Ser  Thr  Met  Cys  Leu  Glu  Gly  Thr  Ala  Gln  Gly  Leu  Val
        1               5                      10                     15
       Val  Asn  Thr  Gly  Asp  Arg  Thr
                          20
```

( 2 ) INFORMATION FOR SEQ ID NO:13:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:13:

```
Leu Phe Ser Gly Thr Asn Ile Ala Ala Gly Lys Ala Leu Gly Ile Val
 1               5                  10                  15
Ala Thr Thr Gly Val Ser Thr
                20
```

( 2 ) INFORMATION FOR SEQ ID NO:14:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:14:

```
Glu Met Ile Met Lys Ser Ile Ile Pro Val Val Met Ala Gly Ile Ile
 1               5                  10                  15
Ala Ile Tyr Gly Leu Val Val
                20
```

( 2 ) INFORMATION FOR SEQ ID NO:15:

( i ) SEQUENCE CHARACTERISTICS:
        ( A ) LENGTH: 17 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

```
Leu Gly Gln Phe Asn Gly Asn Ser Phe Thr Ser Tyr Lys Asp Xaa Ala
 1               5                  10                  15
Asp
```

( 2 ) INFORMATION FOR SEQ ID NO:16:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:16:

```
Asn Ile Lys Asn Val Glu Ile Thr Arg
 1               5
```

( 2 ) INFORMATION FOR SEQ ID NO:17:

( i ) SEQUENCE CHARACTERISTICS:
        ( A ) LENGTH: 21 amino acids
        ( B ) TYPE: amino acid
        ( C ) STRANDEDNESS: unknown ( D ) TOPOLOGY: unknown ( i i ) MOLECULE TYPE: protein ( i x ) FEATURE:
    ( A ) NAME/KEY: Modified-site
    ( B ) LOCATION: 3
    ( D ) OTHER INFORMATION: /note="EITHER VALINE OR ISOLEUCINE CAN BE USED HERE"

( x i ) SEQUENCE DESCRIPTION: SEQ ID NO:17:

```
Thr  Arg  Val  Asp  Phe  Asn  Ala  Lys  Asn  Ile  Leu  Ile  Asp  Asn  Phe  Leu
 1                   5                        10                       15

Glu  Ile  Asn  Asn  Arg
                     20
```

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

TTYTTYACNA CNGTNATHAT        20

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

GAYAAYTTYY TNGARATHAA YAA        23

( 2 ) INFORMATION FOR SEQ ID NO:20:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

CTRTTRAARR ANCTYTADTT RTT        23

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

TTTTTTACAA CCGTGATCAT        20

( 2 ) INFORMATION FOR SEQ ID NO:22:

( i ) SEQUENCE CHARACTERISTICS:
    ( A ) LENGTH: 23 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:22:

TTATTGATTT CTAAAAATT ATC                         23

PURIFIED VACUOLATING TOXIN FROM *HELICOBACTER PYLORI* AND METHODS TO USE SAME

This application is a 371 of PCT/US93/01558, which is a continuation-in-part of U.S. Ser. No. 841,644 filed Feb. 26, 1992 now abandoned.

BACKGROUND OF THE INVENTION

1. Field of the Invention

This invention relates to a *Helicobacter pylori* vacuolating toxin, methods to use the toxin in diagnostic testing for the predisposition to peptic ulceration and gastric malignancy, and methods to use the toxin as a vaccine for providing immunologic protection against *H. pylori* infection.

2. Brief Description of the Background Art

*Helicobacter pylori* is a curved Gram-negative bacterium that is commonly present in the human stomach; once acquired, this organism persists for years or decades (Blaser, M. J. (1990) *J. Infect. Dis.* 161:626–633). Multiple lines of evidence now indicate that *H. pylori* infection nearly universally results in chronic gastritis (Dixon, M. F. (1991) *J. Gastroenterol. and Hepatol.* 6:125–130). Although most persons with *H. pylori*-induced gastritis remain asymptomatic, this condition is a significant risk factor for the development of both peptic ulceration and gastric adenocarcinoma (Peterson, W. L. (1991) *N. Engl. J. Med.* 324:1043–1048, and Nomura, A., Stemmermann, G. N., Chyou, P.-H., Kato, I., Perez-Perez, G. I, and Blaser, M. J., *N. Eng. J. Med.* 1991; 325:1132–6).

The pathogenesis of *H. pylori* infection is not yet well understood. The production of high levels of urease by the organism (Dunn, B. E., Campbell, G. P., Perez-Perez, G. I., and Blaser, M. J. (1990) *J. Biol. Chem.* 265:9464–9469), is thought to be essential for the initiation and maintenance of gastric infection (Eaton, K. A., Morgan, D. R., Krakowka, S. (1989) *Infect. Immun.* 57:1119–1125). Another potential virulence determinant is a toxin that induces vacuolation of eukaryotic cells (Cover, T. L., Halter, S. A., Blaser, M. J. (1992) *Human Pathol.* 23:1004–1010. Functionally active toxin is produced in vitro by 50–60% of *H. pylori* isolates (Leunk, R. D., Johnson, P. T., David, B. C., Kraft, W. G., and Morgan, D. R. (1988) *J. Med. Microbiol.* 26:93–99 and Cover, T. L., Dooley, C. P., and Blaser, M. J. *Infect. Immun.*; 58:603–610 (1990)). Antibodies that neutralize toxin activity are present in sera from *H. pylori*-infected persons, which indicates that the vacuolating toxin activity is relevant in vivo (Leunk, R. D., Ferguson, M. A., Morgan, D. R., Low, D. E., and Simor, A. E. (1990) *J. Clin. Microbiol.* 28:1181–1184 and Cover, T. L., Cao., P., and Blaser, M. J. (1991) *Gastroenterology* 100:A570). Two studies have indicated that the prevalence of infection with toxin-producing *H. pylori* is higher among *H. pylori*-infected persons with peptic ulceration than among infected persons with gastritis alone (Figura, N., Guglielmetti, P., Rossolini, A., Barberi, A., Cusi, G., Musmanno, R., Russi, M., and Quaranta, S. (1989) *J. Clin. Microbiol.* 27:225–226; Goosens, H., Vlaes, L., Lambert, J. P., Glupczynski, Y., Burette, A., and Butzler, J. P. (1991) *Microb. Ecol. Health Dis.* 4:130).

In previous work, the inventors have identified several *H. pylori* proteins that are present in broth culture supernatants with vacuolating toxic activity, but absent or reduced in concentration in supernatants that lack toxic activity (Cover, T. L., Dooley, C. P., and Blaser, M. J. (1990) *Infect. Immun.* 58:603–610). In addition, the inventors have demonstrated that the vacuolating toxin is distinct from *H. pylori* urease (Cover, T. L., Puryar, W., Perez-Perez, G. I., and Blaser, M. J. (1991) *Infect. Immun.* 59:1264–1270). In this application the inventors describe the purification and characterization of the vacuolating toxin from *H. pylori.*

SUMMARY OF THE INVENTION

It is an object of the present invention to provide a substantially pure antigenic composition with vacuolating toxin activity. This antigenic composition can be either purified from natural material or produced recombinantly.

It is a further object of this invention to provide the gene which can be expressed to provide recombinant vacuolating toxin or fragments thereof. The partial DNA sequence of the gene is set out in sequence Id no. 1.

It is an object of the present invention to provide a purified antigenic composition that specifically binds antibodies to the toxin.

It is an object of the present invention to provide a clinical diagnostic test for the presence of infection with toxin-producing *H. pylori*, and thereby identify patients at risk for peptic ulcer disease or gastric malignancy.

It is an object of the invention to provide a protein vaccine which induces high levels of specific antibodies directed against *H. pylori* toxin, and which protects against natural *H. pylori* infection in humans.

It is another object of the invention to provide polyclonal or monoclonal antibodies specific for *H. pylori* toxin, and methods for their use in detecting the toxin, or for therapeutic purposes.

These and other embodiments are accomplished by providing the antigenic compositions, vaccines, methods, antisera or antibodies, and kits disclosed herein.

In one embodiment of the invention, a purified antigenic composition with vacuolating toxin activity (hereinafter termed CB antigen) is extracted from *H. pylori* broth culture supernatant, and has a molecular weight greater than 972, 000 daltons (as determined by gel filtration chromatography under nondenaturing conditions), and an apparent molecular weight of 87,000±300 daltons when denatured (as determined by sodium dodecyl sulfate polyacrylamide gel electrophoresis under reducing conditions (SDS-PAGE). The antigen includes the amino terminal sequence shown is Sequence Id. No. 2, the internal amino acid sequences shown in Sequence Id. Nos. 15–17 and may additionally include the amino acid sequence that is encoded by the nucleotide sequtence as set out in Sequence Id. No. 1. The term CB antigen is defined as the functionally active non-denatured vacuolating toxin; in contrast, the Mr=87,000 protein is a functionally inactive subunit of the CB antigen, which is detected only under denaturing conditions. The term CB antigen will include antigenic fragments of the holotoxin, whether derived from *H. pylori* or synthetically or recombinantly produced. Antigen proteins having substantial homology to CB antigen or fragments thereof may also be used in accordance with the invention. Additionally, CB antigen analogs are also contemplated.

Antiserum or monoclonal antibodies raised against CB antigen may be used to test for the presence of toxin. Test samples are contacted with such antiserum, followed by detection of antibody binding to components of the test samples. Where such binding exceeds a predetermined positive threshold level, the sample is positive for toxin.

CB antigen may be capable of inducing protective immunity against *H. pylori* infection when administered to humans in a nonvirulent manner. Hence, the antigen may be used in combination with a suitable adjuvant, as a vaccine against future *H. pylori* infection.

In one aspect of the invention, CB antigen is used in methods for the detection of anti-toxin antibodies. The purified toxin is contacted with samples of body fluids suspected of containing antitoxin antibodies. Following such contacting, known methods are used to determine the extent of antigen-antibody complex formation. When formation of the complex exceeds a predetermined positive threshold value, the test is positive for presence of anti-toxin antibodies.

Preferred techniques for detecting formation of antigen-antibody complexes include, but are not limited to, enzyme-linked immunosorbent assay (ELISA), indirect immunofluorescence assay, latex agglutination, and liposome-based assay. Alternatively, a Western blot technique may be used, in which case the bands are detected by visual inspection, and substantial appearance of dark bands may be taken as a positive indication. The extent of detection of the antigen/antibody complex which should be considered a positive signal (i.e., an indication that the test sample includes toxin-specific antibody) depends upon the detection means chosen, but may be defined generically as a value greater than the mean plus 1 interval of standard deviation from the results observed with samples from a negative control group, all other parameters (dilution of sample, time of incubation, etc.) being held constant. In some embodiments where higher specificity is desired, the mean plus two or mean plus three standard deviations may be utilized. The negative control group should consist of individuals who are known to be free of *H. pylori* infection.

In one aspect of the invention, kits are provided which include the antigenic compositions within the scope of the invention, and which further include means for detecting the presence of any immunoglobulin in a test sample which may become bound to antigens in said compositions.

Additionally, diagnostic tests for *H. pylori* infection can be developed based on primer directed amplification of nucleic acid samples of subjects. More specifically, synthetic oligonucleotides selected from the nucleotides set out in sequence Id. no 1 can be used in a polymerase chain reaction to amplify *H. pylori* toxin to detectable levels.

BRIEF DESCRIPTION OF THE DRAWINGS

FIG. 4 shows neutralization of *H. pylori* vacuolating toxin activity by antiserum raised against the purified denatured $Mr=87,000$ protein subunit. Preimmune serum and antiserum raised against the purified $Mr=87,000$ *H. pylori* protein subunit were tested for toxin-neutralizing activity. The neutral red uptake induced by crude concentrated broth culture supernatant from *H. pylori* 60190 is indicated by the dashed line. At a dilution of 1:64, the antiserum completely neutralized toxin activity, whereas the preimmune serum failed to neutralize toxin activity.

FIG. 5 shows detection of the vacuolating toxin in *H. pylori* supernatants. Concentrated culture supernatants from 8 $tox^+$ *H. pylori* strains and 8 $tox^-$ strains were diluted 1:100 in carbonate buffer and tested in an ELISA for reactivity with antiserum to the denatured $Mr=87,000$ protein subunit (1:10,000 dilution). $Tox^+$ supernatants produced significantly higher optical density values than $tox^-$ supernatants ($0.614\pm0.11$ versus $0.046\pm0.01$, $p<0.0001$).

FIG. 6 shows serologic recognition of the purified *H. pylori* toxin (CB antigen) by human sera. Sera from twenty *H. pylori*-infected persons and twenty uninfected persons were diluted 1:100 and tested in an ELISA for IgG reactivity with the purified CB antigen (15 ng/microtiter well). Sera from *H. pylori*-infected persons recognized the purified toxin significantly better than sera from uninfected persons (mean optical densities $0.424\pm0.06$ and $0.182\pm0.02$, respectively, $p=0.0009$).

DETAILED DESCRIPTION OF THE INVENTION AND BEST MODE

Figure 1A:
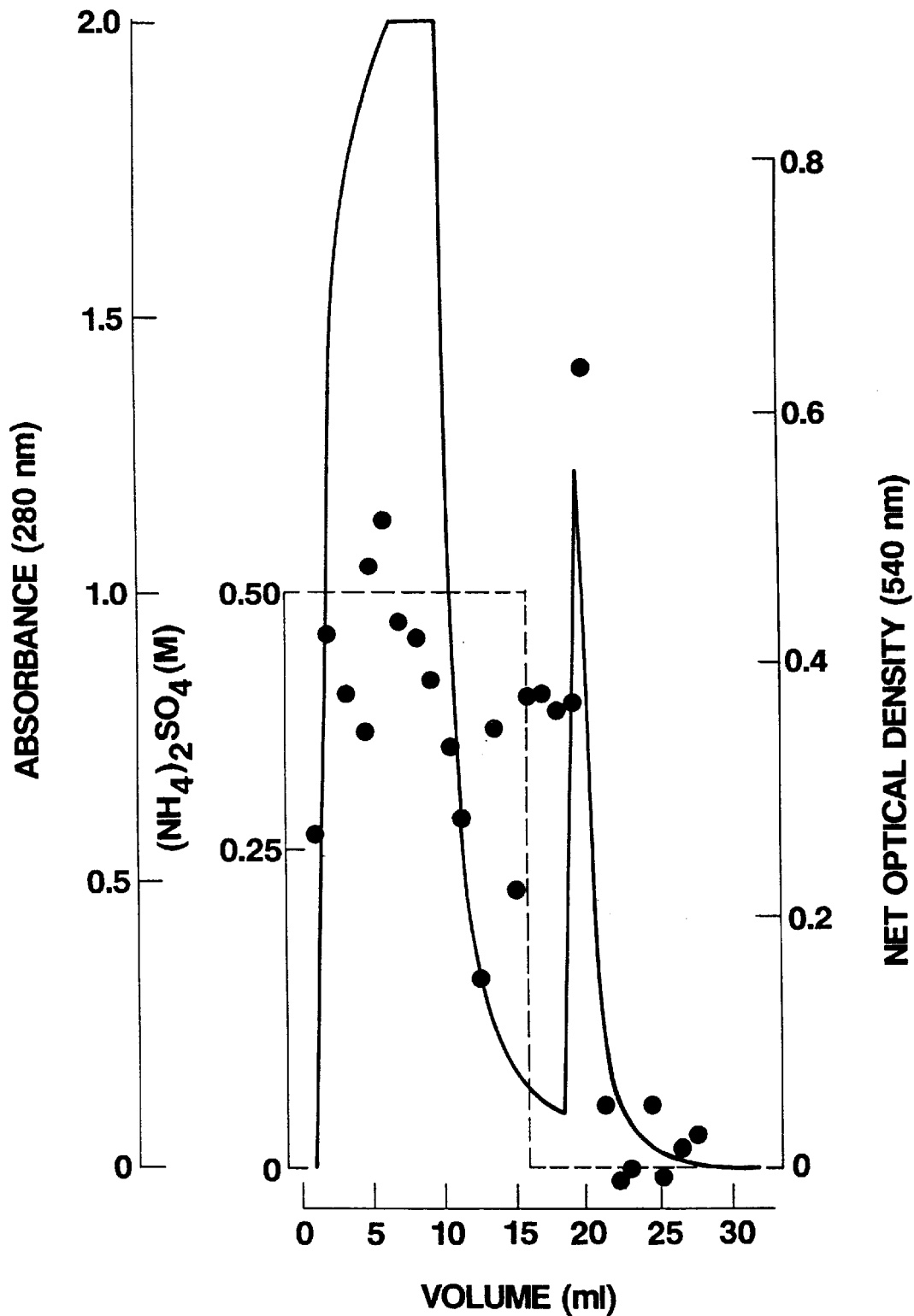
FIG. 1A–1C shows column chromatography of *H. pylori* vacuolating toxin. Column eluates were monitored for absorbance at 280 nanometers (solid lines), and salt concentrations are indicated by the dashed lines. The vacuolating cytotoxin activity of fractions was assayed using the neutral red assay and is expressed as net optical density (solid circles). A) PHENYLSUPEROSE (Pharmacia) chromatography of ammonium sulfate-precipitated supernatant proteins. The presence of ammonium sulfate (0.5M) in the buffer of early fractions (volume 1–15 ml) contributed to the neutral red uptake induced by these fractions (Cover, T. L., Puryear, W., Perez—Perez, G. I., Blaser, M. J. (1991) *Infect. Immun.* 59:1264–70). B, the eluted peak from A was applied to a SUPEROSE 12 (Pharmacia) column, and toxic activity was detected in the void volume. C, fractions with toxic activity eluted from the SUPEROSE 12 (Pharmacia) column were applied to a MONO Q (Pharmacia) column, and toxic activity was eluted by a linear gradient of NaCl.
Figure 1B:
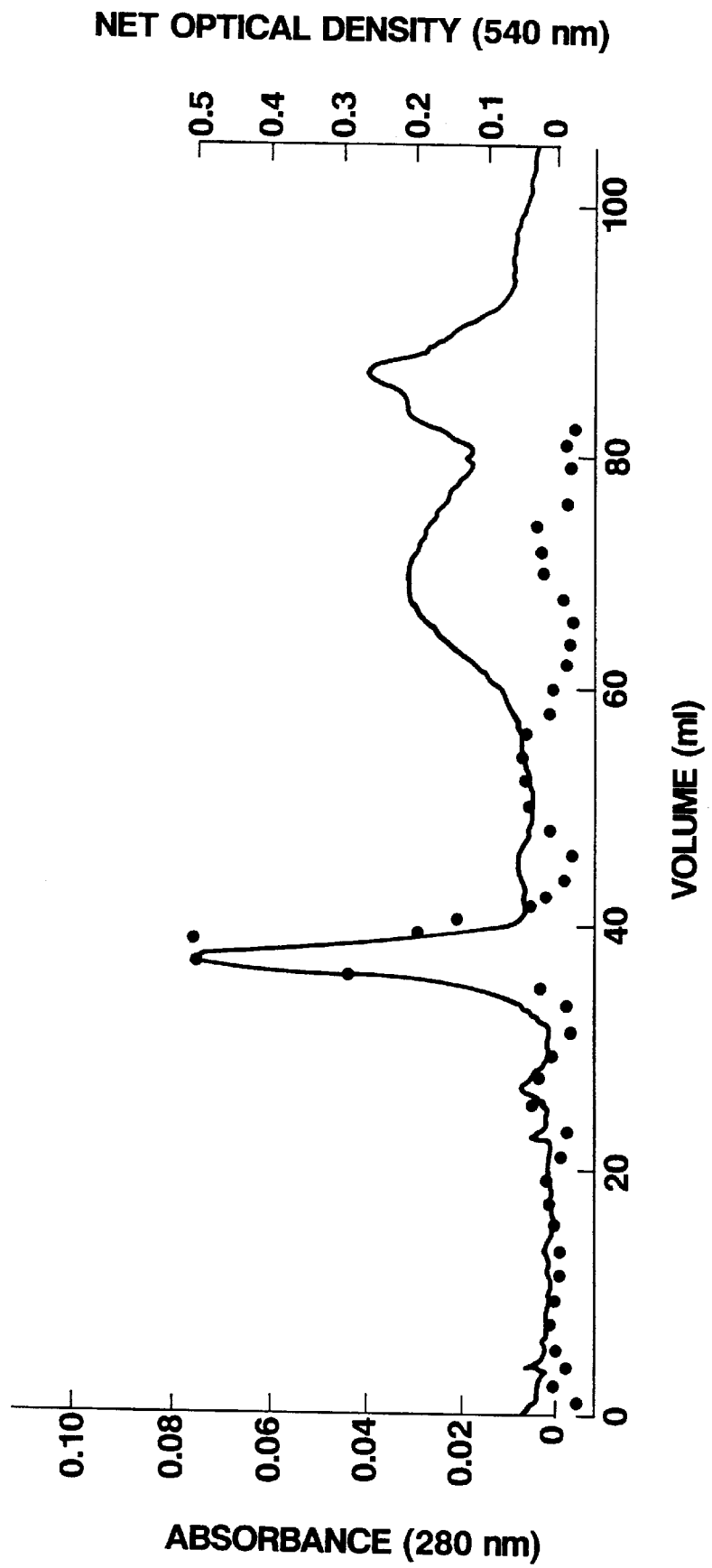
Figure 1C:
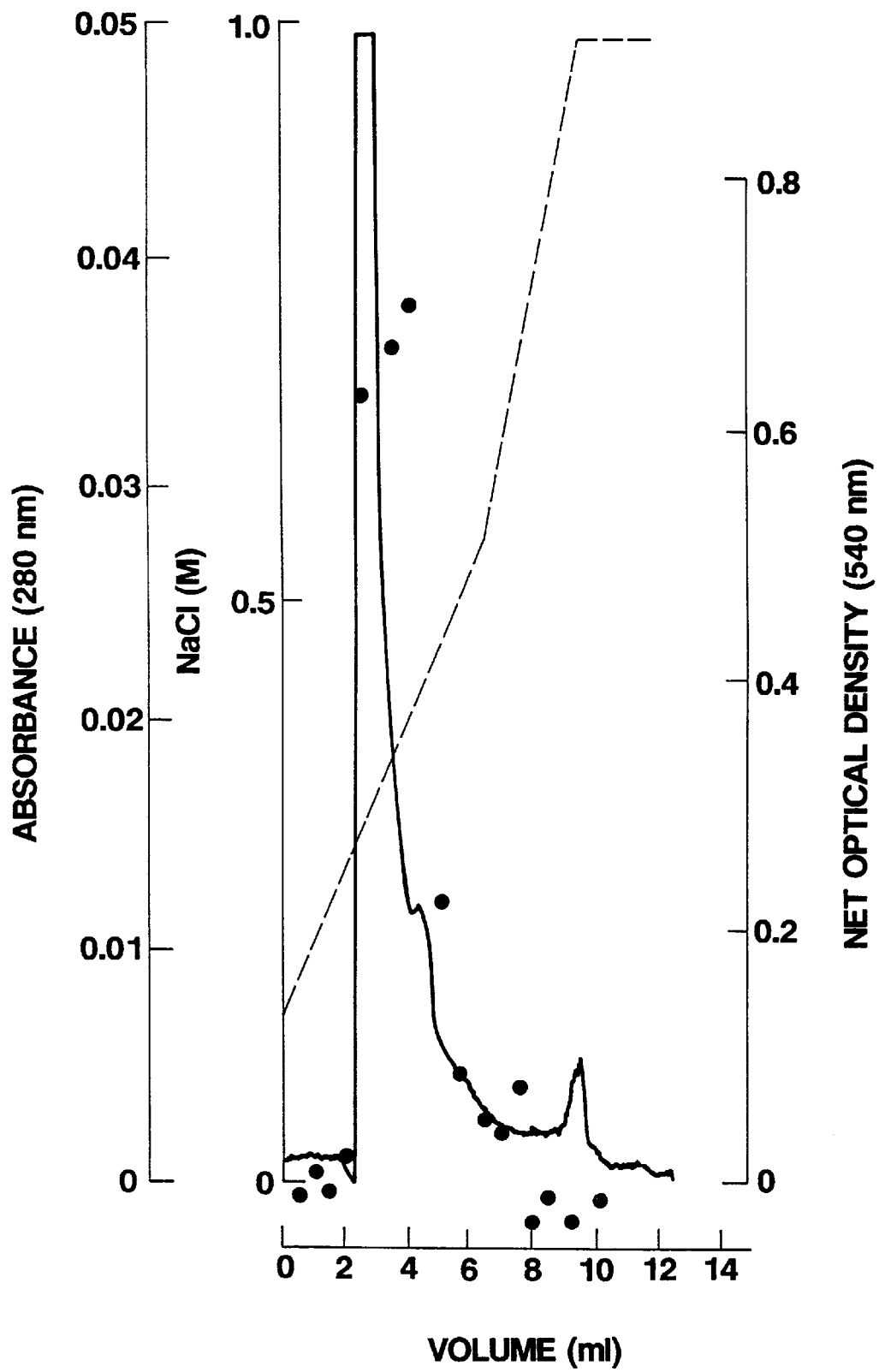

This work represents the first purification to homogeneity of the vacuolating toxin of *H. pylori*. The toxin was isolated from broth culture supernatant by ammonium sulfate precipitation, followed by hydrophobic interactive chromatography, gel filtration chromatography, and anion exchange chromatography. The term substantially pure means that the CB antigen is present in the antigenic composition at a concentration, relative to the other *H. pylori* products, higher than that in the *H. pylori* broth culture supernatant.

These procedures resulted in recovery of a purified, functionally active toxin, with molecular weight greater than 972,000 daltons under non-denaturing conditions (CB antigen). The purification of this protein was associated with a greater than 5000-fold increase in specific activity of the toxin. Analysis of the purified toxin (CB antigen) by SDS- PAGE under denaturing, reducing conditions demonstrated the presence of a single band migrating at 87,000 daltons. By ELISA, antiserum to the denatured Mr=87,000 protein subunit reacted with tox⁺ H. pylori supernatants to a significantly greater extent than with the tox⁻ H. pylori supernatants. In addition, antiserum to the denatured Mr=87,000 protein subunit neutralized the vacuolating toxic activity of H. pylori 60190, as well as the toxins produced by other H. pylori strains. Altogether, these data support the role of the CB antigen in vacuolating toxin activity, and indicate that the toxins produced by various H. pylori strains are antigenically related.

Western blot analysis demonstrated that the denatured Mr=87,000 protein subunit appears related to a band identified in our previous analysis of tox$^{30}$ H. pylori culture supernatants (originally reported as Mr=82,000) (Cover, T. L., Dooley, C. P., and Blaser, M. J. (1990) Infect. Immun. 58:603–610). Our previous study of tox⁺ H. pylori supernatants also identified an Mr=128,000 protein, which was recognized by sera from patients with peptic ulceration more frequently than by H. pylori-infected persons without ulcer disease (Cover, T. L., Dooley, C. P., and Blaser, M. J. (1990) Infect. Immun. 58:603–610; Crabtree, J. E., Taylor, J. D., Wyatt, J. I., Heatley, R. V., Shallcross, T. M., Tompkins, D. S., and Rathbone, B. J. (1991) Lancet 338:332–335). The current study indicates that the Mr=128,000 protein is not required for expression of vacuolating toxin activity, and is not immunologically cross-reactive with the Mr=87,000 protein subunit.

Any sample suspected of containing antibodies may be tested in accordance with The methods set forth herein. Preferably, the samples to be tested are bodily fluids such as blood, serum, urine, tears, saliva and the like. In addition to human samples, samples may be taken from mammals such as non-human primates, horses, swine, etc. Due to the sensitivity of the test described, it is possible to dilute the sample prior to testing. Dilution may proceed by addition of any fluid compatible with each of the sample, the antibodies to be tested, and the antigenic composition. Serum, when used as the sample, may, for example, be diluted with one or more fluids selected from the group consisting of phosphate-buffered saline, pH 7.0–7.4 (hereinafter, "PBS"), PBS-containing Tween 20 (hereinafter,"PBS T"); PBS T with thimerosal (hereinafter, "PBS"TT), PBS TT with gelatin (hereinafter, "PBS TTG"), and PBS TTG with bovine gamma globulin (hereinafter, "PBS TTGG"). Dilutions, when testing for IgG antibody, may be as high as a ratio from about 1:100 to about 1:1000. Although samples also may be tested for IgA and IgM antibodies, IgG tests are preferred.

Preferred diluents and dilution ratios may vary according to the sample being tested. Urine, for instance, is already relatively dilute and may not need to be diluted further. However, it may not be necessary to concentrate urine as is often necessary with other assays. Prior to testing, the pH of urine is preferably adjusted to between about 7.0 and 7.4, the preferred pH for antibody function.

While dilution of sample is not required, it is believed that dilution reduces the possibility that significant antigen/antibody complexes will be formed in the absence of H. pylori specific antibodies. The extent of dilution should be taken into account in adjusting the threshold level of antigen/antibody complex which should be considered a positive signal.

While the present disclosure provides an easy method for obtaining the purified toxin (CB antigen) from the deposited H. pylori strain, it is emphasized that this antigen is common to a number of H. pylori strains. While the deposited strain and the description of the present specification provide an easy manner of isolating this antigen, it is emphasized that the present invention broadly encompasses use of the antigen regardless of the source or method whereby it is derived, such as for example by recombinant production.

Before contacting a test sample with antigenic compounds in accordance with the invention it is preferred (but not necessary) that the antigenic composition be immobilized using conventional techniques. In one alternative embodiment, liposome-based assays may be used as described in more detail below. For conventional immobilization, polystyrene plates, for example, may be incubated with antigenic suspensions made in accordance with the invention. Alternatively, for example, antigens isolated as protein bands on electrophoretic gel may be transferred to a nitrocellulose sheet by known methods. See Towbin et al., Proc. Nat'l. Acad. Sci., 76:4350–54 (1979); Burnette et al., Biochem., 112:95–203 (1981). Numerous other techniques are known in the art for binding antigens to substantially inert substrates.

Bound antigens in accordance with the invention are preferably contacted with a dilute fluid which includes the sample to be tested for presence of antibody to H. pylori. The antigen and sample are preferably incubated for at least 5 to 15 minutes. Less time is needed when incubation proceeds at or near human body temperature, about 37° C. Incubation at other temperatures, for instance 4° C., is also proper, but generally requires additionally incubation time. Preferred incubation time at 37° C. is from about 5 minutes to about 90 minutes. Rapid assays can also be performed at room temperature. The bound antigens should then be rinsed to remove any unbound antibodies, i.e., those which are not specific for the antigens. Preferably, rinsing proceeds with a buffer solution such as PBS T, PBS TT or Tris/Tween/Sodium chloride/azide. Multiple rinsing are preferred.

During incubation, H. pylori specific antibodies bind to the immobilized antigens to create antigen/antibody complexes. All unbound antibodies are substantially removed during the rinsing procedure. Due to the high specificity of the antigens of the invention, antibodies which are not specific for H. pylori are substantially removed by the rinsing. Naturally, if the tested sample did not contain H. pylori specific antibodies, the immobilized antigens would be substantially free of human antibody, and subsequent testing for antigen/antibody complexes should not indicate a substantial presence of such complexes. On the other hand, if the tested sample were rich in H. pylori specific antibodies, these antibodies should have bound to the immobilized antigens to form a large quantity of antigen/antibody complex for subsequent detection.

Detection of antigen/antibody complex may be achieved by a wide variety of known methods. Preferred methods include but are not limited to enzyme-linked immunosorbent assay, latex agglutination, Western blot technique or indirect immunofluorescence assay.

Typically, the H. pylori specific antibodies complexed with immobilized antigen are detected by contact with labeled or otherwise detectable second antibodies specific for the immunoglobulin being tested for. If the test sample is human sera, for example, the detectable second antibody is specific for human immunoglobulin. The labeled second antibodies may be specific for any human antibody, preferably of the IgG or IgA type, most preferably IgG. When acute sero-conversion is suspected, an IgM test using a labeled second antibody specific for IgM may be appropriate. The second antibodies are preferably incubated with the immobilized antigens for about 5 minutes to about two hours, preferably 30 minutes to 60 minutes at a temperature of about 20° C. to about 37° C. Then, the antigens are washed with a buffer solution (preferably multiple times) in order to remove all unbound labeled antibody. The washing will remove substantially all labeled antibody except that which has bound to immunoglobulin present on the antigens. Of course, substantially the only human immunoglobulin present at this point should be *H. pylori* specific antibody. Hence, the presence of *H. pylori* specific antibody may be indirectly measured by determining the presence or absence of the labeled second antibody.

There are many known techniques for detecting the label, which vary with the type of label used. For instance, fluorescein-labeled antibody may be detected by scanning for emitted light, at the characteristic wavelength for fluorescein. Alternatively, an enzyme label is detected by incubation with appropriate substrates and detection of an enzyme activity, preferably activity resulting in a color change. Such activity can be determined by visual inspection or can be read automatically by a spectrophotometer set at the appropriate wavelength.

Alternatively, the enzyme label may be horseradish peroxidase and the substrate may be $H_2O_2$ and 2,2'-azinobis(3-ethylbenzothiazoline-6-sulfonic acid) which produces in the presence of the enzyme, a compound detectable by a spectrophotometer set at 414 nm.

In Western blotting, the positive signal may be detected when an enzyme is conjugated to the second antibody. Incubation with appropriate substrate enzymatically produces a color product in the immediate vicinity of the antigenic band resolved by this process. The presence of a reactive band may be detected by visual inspection. In an indirect immunofluorescence assay, fluorescein-labeled second antibodies may be detected by flurorescence-activated detectors, or by visual inspection.

A liposome-based assay may involve the presence of fluorescein, an enzyme or a substrate inside a liposome onto whose surface *H. pylori* antigens are expressed. These liposomes are incubated with a diluted body fluid sample to be tested, and are thoroughly washed. Any liposome with immunoglobulins on their surface forming an antigen/antibody complex may be recognized by attaching a second antibody, specific to the immunoglobulin being tested for, onto the inside walls of a polystyrene tube containing the liposomes. Liposomes having antibody bound to their surfaces will become immobilized on the tube walls, and non-immobilized liposomes will be washed away. The liposomes can by lysed with, for instance, detergent, or complement, and the enzyme or substrate that was in the interior is now free to react with the complementary substrate (or enzyme) in the solution in the tube. Enzymatic activity, preferably a color change reaction could be detected by visual inspection or spectrophotometric color determination. Enzymatic activity beyond the predetermined positive threshold indicates the presence of *H. pylori* specific antibodies.

The sensitivity and specificity of the antibody detection in accordance with the present invention have been determined using serum obtained from persons from defined populations. By ELISA, IgG antibodies to the purified toxin (CB antigen) have been identified in sera from *H. pylori*-infected persons. The ELISA optical density values produced by sera from approximately 50% of *H. pylori*-infected persons exceeded the range produced by sera from uninfected persons. This suggests that approximately 50% of *H. pylori*-infected persons are infected with strains of *H. pylori* that produce the toxin. Similarly, approximately 50% of *H. pylori* strains produce the toxin in vitro. (Leunk, R. D., Johnson, P. T., David, B. C., Kraft, W. G., and Morgan, D. R. (1988) *J. Med. Microbiol.* 26:93–99; Cover, T. L., Dooley, C. P., and Blaser, M. J. (1990) *Infect. Immun.* 58:603–610).

In this application results are expressed as the mean±SEM. Optical density values were compared using the two-tailed Student's t test for independent variables.

Additionally, detection of nucleic acid in specimens comprising body fluids or tissues can be difficult because of the small quantity of nucleic acid present or because of the presence in the specimen of other interfering materials, including DNA or RNA from a different source. These limitations may be overcome by employing an analytic method referred to as the polymerase chain reaction (PCR) technique. By this technique, selective enrichment of a specific DNA sequence can be achieved by exponential amplification of the target sequence. Mullis, et al., *Met. Enzymol.*, 155, 335 (1987). A method to detect *H. pylori* toxin is provided by using primer directed amplification of oligonucleotides selected from the DNA sequence set out in sequence Id. number 1, to amplify a sample of *H. pylori* toxin producing nucleic acids to a detectable level.

To facilitate PCR amplification, pairs of oligonucleotide primers may be employed as described in U.S. Pat. No. 4,683,202 (hereby incorporated by reference). The primers are designated to hybridize with sequences that flank the target DNA. Following in vitro amplification, the amplified target sequence is detected by a hybridizing probe. For example, this analytical procedure has been used for the direct detection of HIV-1 as described by Ou, et al., *Science*, 238, 295–97 (1988). The amplification cycles are facilitated by using a polymerase which is thermally stable in incubations up to 95 degrees centigrade, as described by Saiki, et al., *Science*, 239, 487–91 (1988).

Certain embodiments of the present invention used synthetic oligonucleotide sequences as primers. These sequences can be prepared by well known chemical procedures, and commercially available DNA synthesizers can also be used. For example, the required sequence can be prepared by the synthesis method described by Beaucage, et al., *Tetrahedron letters*, 22: 1859–62 (1981). Another method for the synthesis of oligonucleotide on the solid support is described in U.S. Pat. No. 4,458,066. Automated DNA synthesis apparatus can be used such as the DNA synthesizer sold by Applied Biosystems.

More specifically, the oligonucleotide sequences of the probe sequences are represented by the standard letter abbreviations in which the nucleotide are designate as follows: A for adenosine, T for thymidine, G for guanosine, and C for cytosine and N for unknown. These strands are represented in a standard 5' prime to 3' prime orientation. Abbreviations used in the degenerate primers are shown in Table 3.

EXAMPLE 1

Purification of Toxin

*H. pylori* 60190 (ATCC 49503), a previously described toxin-producing strain, was used as the source for toxin purification. *H. pylori* 60190 was cultured for 48 hours at 37° C. in Brucella broth containing 0.5% charcoal (untreated, granular 8–20 mesh, Sigma) in an ambient atmosphere containing 5% $CO_2$ (Cover, T. L., Puryear, W., Perez—Perez, G. I., and Blaser, M. J. (1991) Infect. Immun. 59:1264–1270). The culture was centrifuged at 10,000 g for 20 minutes, and proteins present in the supernatant were precipitated with a 50% saturated solution of ammonium sulfate. After centrifugation at 10,000 g for 15 minutes, the pellet was resuspended in 60 mM Tris-HCl (pH 7.7).

Hydrophobic interactive chromatography was performed on a PHENYLSUPEROSE HR 5/5 column (Pharmacia LKB Biotechnology Inc., Piscataway, N.J.) with buffer containing 60 mM Tris-HCl and 0.5M ammonium sulfate (pH 7.7), and proteins were eluted with 60 mM Tris HCl (pH 7.7). Size exclusion chromatography was performed on a SUPEROSE 12 HR 16/50 column (Pharmacia) with buffer containing 60 mM Tris-HCl and 0.1M NaCl (pH 7.7) at a flow rate of 0.12 ml/minute. Anion exchange chromatography was performed on a MONO-Q HR 5/5 column (Pharmacia) in 20 mM Tris (pH 7.7). Proteins were eluted with 20 mM Tris containing a linear gradient of 0.3M NaCl to 0.6M NaCl over 10 milliliter. Column eluates were monitored for UV absorbance at 280 nanometers.

HeLa cells were cultured in Eagle's modified minimal essential medium containing 10% fetal bovine serum (MEM-FBS) in 96-well plates, as previously described (Cover, T. L., Dooley, C. P., and Blaser, M. J. (1990) Infect. Immun. 58:603–610). Toxin preparations were serially diluted in MEM-FBS, and 10 microliter aliquots were incubated with adherent cells and 90 microliters of medium in 96-well plates for 18 hours at 37° C. Cell vacuolation was then quantitated spectrophotometrically using a neutral red uptake assay, as previously described (Cover, T. L., Puryear, W., Perez—Perez, G. I., and Blaser, M. J. (1991) Infect. Immun. 59:1264–1270). The titer of toxic activity in a sample was defined as the maximum dilution of the sample that produced an optical density value greater than or equal to three SD above that produced by medium alone. The specific activity of a sample was defined as the ratio of the reciprocal toxin titer to the protein concentration (in mg/ml). For determination of specific activity, MEM-FBS was supplemented with ammonium chloride (10 mM), a concentration previously shown to potentiate toxic activity (Cover, T. L., Puryear, W., Perez—Perez, G. I., and Blaser, M. J. (1991) Infect. Immun. 59:1264–1270), and which approximates the concentration of ammonium ion in the gastric juice of H. pylori-infected humans (Marshall, B. J., and Langton, S. R. (1986) Lancet i:965–966).

Protein concentrations were measured using either QUANTIGOLD reagent (Diversified Biotech, Newton Centre, Mass.) or the BCA protein assay reagent kit (Pierce, Rockford, Ill.), depending on the concentration of samples, and albumin was used as a standard. SDS-PAGE was performed in a modified Laemmli gel system as described by Ames (Ames, G. F.-L (1974) J. Biol. Chem 249:634–644), and proteins were resolved in gels using the silver stain of Oakley et al. (Oakley, B. R., Kirch, D. R., and Morris, N. R. (1980) Anal. Biochem. 105:361–363). Molecular weight standards included rabbit muscle phosphorylase b (97,400), bovine serum albumin (66,200), hen egg white ovalbumin (45,000), bovine carbonic anhydrase (31,000), and soybean trypsin inhibitor (21,500) (Biorad, Richmond, Calif.).

Figure 2:
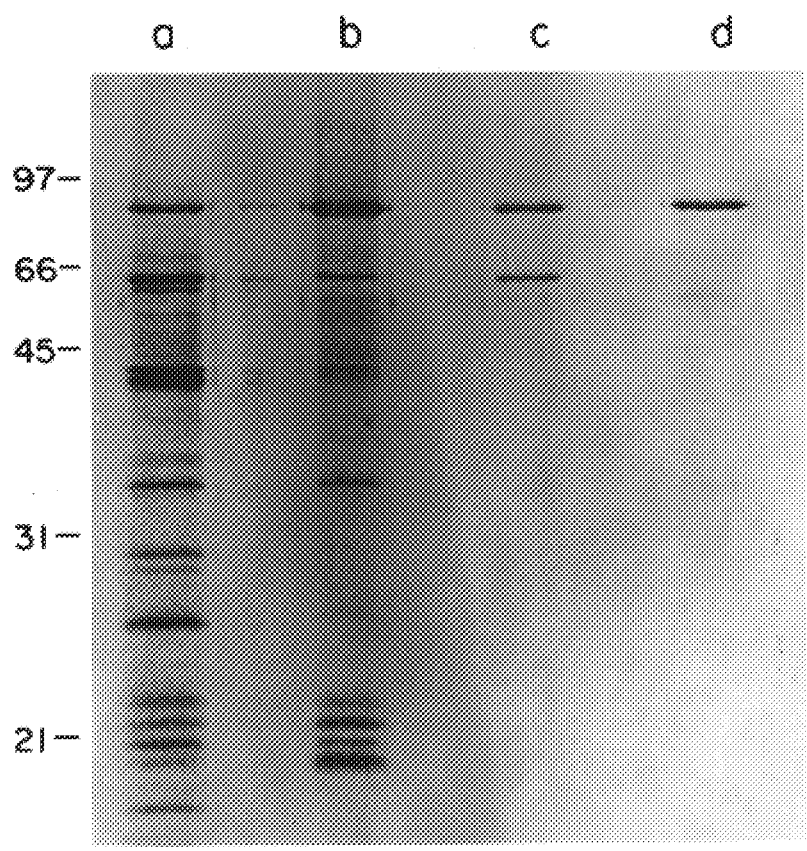
FIG. 2 shows sodium dodecyl sulfate-polyacrylamide gel electrophoresis (12% acrylamide) of *H. pylori* toxin (CB antigen) under denaturing, reducing conditions. Lanes are: a, proteins precipitated from a broth culture supernatant of *H. pylori* 60190 by a 50% saturated solution of ammonium sulfate; b, toxin partially purified by hydrophobic interactive chromatography; c, toxin partially purified by gel filtration chromatography; d, purified CB antigen after anion exchange chromatography, visualized as an $Mr=87,000$ band under denaturing, reducing conditions. Chromatography conditions were as described in the text. The migrations of marker proteins of known molecular weight (in kilodaltons) are shown at left.
Figure 3:
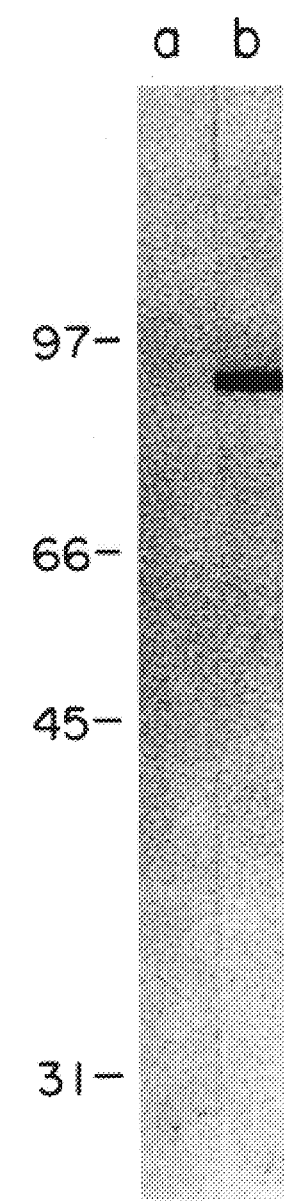
FIG. 3 shows Western blot recognition of the $Mr=87,000$ protein band by immune rabbit serum. Proteins precipitated from the broth culture of *H. pylori* 60190 by a 50% saturated solution of ammonium sulfate were electrophoresed on a 10% acrylamide gel, transferred to a nitrocellulose paper, incubated with 1:10,000 dilutions of rabbit sera, and the antigens resolved. Lane a, preimmune serum. Lane b, antiserum produced against the purified denatured $Mr=87,000$ *H. pylori* protein subunit. The antiserum recognized only the $Mr=87,000$ band.

The purification of the vacuolating toxin of H. pylori involved ammonium sulfate precipitation of proteins present in broth culture supernatant, followed by sequential hydrophobic interactive, gel filtration, and anion exchange chromatography, as described above. SDS-PAGE under denaturing conditions, and silver staining indicated purification to homogeneity of an Mr=87,000±300 protein subunit (FIG. 2). As summarized in Table 1, analysis of the specific activities at each stage in the purification process indicated that the toxin (CB antigen) was purified more than 5000-fold from the unconcentrated broth culture supernatant and 25-fold from the ammonium sulfate precipitate. Thus, a substantially pure preparation was obtained in which the toxin was present at a concentration, relative to other H. pylori products, higher than that in H. pylori broth culture supernatant. The recovery of the purified toxin was 8 micrograms per liter of culture supernatant, which represented less than 5% of the toxic activity present in the original unconcentrated supernatant.

In addition to the above discussed purification method, substantially pure toxin can be produced by substituting a SUPEROSE 6 (Pharmacia) column in place of a SUPEROSE 12 (Pharmacia) column. Similarly, other modifications in the purification method, can be employed by one skilled in the art. For example, additives to prevent protein degeneration may be included, such as PMSF, DTT, EDTA AND 10% glycerol.

TABLE 1

Purification of vacuolating cytotoxin activity from H. pylori strain 60190

| Purification step | Specific activity | Purification (-fold) |
| --- | --- | --- |
| Broth culture supernatant | 4.5 ± 1.5 | 1 |
| Ammonium sulfate precipitate | 950 ± 530 | 211 |
| Phenylsuperose chromatography | 2000 ± 310 | 444 |
| SUPEROSE 12 chromatography | 16,000 ± 5900 | 3556 |
| MONO Q chromatography | 24,000 ± 5600 | 5333 |

[1]The results of three purification are shown (mean ± SEM). Chromatography conditions were as specified in the text. Specific activity was defined as the ratio of the reciprocal titer of toxic activity to the protein concentration (in mg/ml).

EXAMPLE 2

Characterization of the CB Protein.

After partial purification by hydrophobic interactive and gel filtration chromatography, the toxin preparation was electrophoresed under denaturing conditions on a 7% acrylamide gel. The Mr=87,000 band was excised and eluted from the gel and 0.7M ammonium bicarbonate was added. The solution was then applied to a PHENYLSUPEROSE HR 5/5 column (Pharmacia), and eluted with distilled water. Amino-terminal amino acid sequencing was performed as described previously (Pei, Z., Ellison, R. T., III, Lewis, R. V., and Blaser, M. J. (1988) J. Biol. Chem. 253:6416–6420), and the National Biomedical Research Foundation and Swiss-Prot data bases were searched for potential homologies with known proteins. Amino acid composition analysis was performed as described by Jones (Jones, B. N. (1981) J. Liq. Chromatogr. 4:565:586).

The amino acid composition of the purified, denatured Mr=87,000 protein subunit is as follows (in mole %): Asx 14.8, Glx 9.6, Ser 9.3, His 1.5, Gly 13.0, Thr 6.7, Arg 3.5, Ala 8.1, Tyr 3.8, Met 2.3, Val 6.7, Phe 4.6, Ile 6.7, Leu 9.3 (Lys, Trp, Pro, and Cys not determined). Based on two determinations, the sequence of the 23 N-terminal amino acids is as shown in Table 2 (Sequence Id. No. 2). The N-terminal sequence is rich in hydrophobic amino acids, is uncharged, and has a predicted isoelectric point of 5.83. Garnier-Robson structural predictions indicate that this part of the sequence is associated with a 100% extended conformation.

A comparison between the N-terminal sequence of the Mr=87,000 protein subunit and other known proteins indicated no strong homology. However, there was partial homology between the N-terminus of the Mr=87,000 protein subunit and internal sequences of numerous other known proteins, many of which were involved in transport processes (Table 2) (Salkoff, L., Butler, A., Scavarda, N., and Wei, A. (1987) *Nucleic Acids Res.* 15:8569–72; Rogart, R. B., Cribbs, L. L., Muglia, L. K., Kephart, D. D., and Kaiser, M. W. (1989) *Proc. Natl. Acad. Sci. USA* 86:8170–74; Takeyasu, K., Tamkun, M. M., Renaud, K J., and Fambrough, D. M. (1988) *J. Biol. Chem.* 263:4347–54; Hesse, J. E., Wieczorek, L., Altendorf, K., Reicin, A. S., Dorus, E., and Epstein, W. (1984) *Proc. Natl. Acad. Sci. USA* 81:4746–50; Mandel, M., Moriyama, Y., Hulmes, J. D., Pan, Y-C. E. Nelson, H., and Nelson, N. (1988) *Proc. Natl. Acad. Sci. USA* 85:5521–24; Hiles, I. D., Gallagher, M. P., Jamieson, D. J., and Higgins, C. F. (1987) *J. Mol. Biol.* 195:125–42; and Szkutnicka, K., Tschopp, J. F., Andrews, L., and Crillo, V. P. (1989) *J. Bacteriol* 171:4486–93; Hawkins, A. R., Lamb, H. K., Smith, M., Keyte, J. W., and Roberts, C. F. (1988) *Mol. Gen. Genet.* 214:224–231; Goldrick, D., Yu, G.-Q., Jiang, S. Q., and Hong, J.-S. (1988) *J. Bacteriol* 170:3421–3426). Based on hydropathy plot analyses, the sequences homologous to the *H. pylori* Mr=87,000 protein subunit were frequently hydrophobic, membrane-spanning segments. In addition to the proteins listed in Table 2, there was partial homology with the calcium channel release protein from pig (Harbitz, I., Chowdhary, B., Thomsen, P. D., Davies, W., Kaufmann, W., Kran, S., Gustavsson, I., Christensen, K., and Hauge, J. G. (1990) *Genomics* 8:243–248), the kainate gated ion channel precursor from rat (Hollmann, M., O'Shea-Greenfield, A, Rogers, S. W., and Heinemann, S. (1989) *Nature* 342:643–8), general amino aid permease from *Saccharomyces cerevisiae* (Jaunizux, J.-C., and Grenson, M. (1990) *Eur. J. Biochem.* 190:39–44), arginine permease from *S. cerevisiae* (Hoffmann, W. (1985) *J. Biol Chem.* 260:11831–7), lactose permease from *E. coli* ( D. E., Groneborn, B., and Muller-Hill, B. (1980) *Nature* 283:541–545), and the mannose permease EII-P MAN segment from *E. coli* (Erni, B., Zanolari, B., and Kocher, H. P. (1987) *J. Biol. Chem* 262:5238–47). The partial homology between the N-terminus of the Mr=87,000 protein subunit and different regions of multiple families of ion channel and transport proteins suggests that this relationship may be significant.

TABLE 2

Sequence homology between *H. pylori* vacuolating toxin and ion channel or transport proteins

*H. pylori* Mr = 87,000 protein subunit (Sequence Id. 2)

| Start | | | | | | | | | | | | | | | | | | | Finish |
|---|---|---|---|---|---|---|---|---|---|---|---|---|---|---|---|---|---|---|---|
| 1 A | F | F | T | T | — | V | I | — | I | P | A | I | V | G | G | I | A | T | G T A V G T 23 |
| * | * | * | * | * | | * | : | | : | * | * | * | | | | : | : | | |

Sodium channel: Drosophila (Sequence Id. 3)

| 1355 A | F | F | T | T | — | V | F | G | L | E | A | I | V | K | I | V | G | L | R Y H Y F T 1378 |
|---|---|---|---|---|---|---|---|---|---|---|---|---|---|---|---|---|---|---|---|
| * | * | * | * | * | | : | * | | * | : | | : | : | | | | | | : : |

Sodium channel protein i cardiac: rat (Sequence Id. 4)

| 1752 L | F | F | T | T | Y | I | I | — | I | S | F | L | I | V | V | N | M | Y | I A I I L E 1775 |
|---|---|---|---|---|---|---|---|---|---|---|---|---|---|---|---|---|---|---|---|
| * | * | * | : | * | | : | | | : | : | | | | * | * | | : | * | : * |

Na+-K+-transporting-ATPase alpha: chicken (Sequence Id. 5)

| 241 A | F | F | S | T | — | N | C | — | V | E | G | T | A | V | G | I | V | I | S T G D R T 263 |
|---|---|---|---|---|---|---|---|---|---|---|---|---|---|---|---|---|---|---|---|
| | : | | | | | : | | | * | * | : | | : | * | * | : | : | : | : * * : |

H+-K+-transporting-ATPase b chain: *E. coli* (Sequence Id. 6)

| 256 V | A | L | L | V | — | C | L | — | I | P | T | T | I | G | G | L | L | S | A S A V A G 278 |
|---|---|---|---|---|---|---|---|---|---|---|---|---|---|---|---|---|---|---|---|
| | : | | | | | * | | | * | * | | : | : | : | * | * | | : | : : |

H+-transporting ATPase proteolipid chain: bovine (Sequence Id. 7)

| 50 E | M | I | M | K | — | S | I | — | I | P | V | V | M | A | G | I | I | A | I Y G L V V 72 |
|---|---|---|---|---|---|---|---|---|---|---|---|---|---|---|---|---|---|---|---|
| * | * | : | | : | | * | * | | * | * | | | * | | | * | * | * | : |

Oligopeptide permease: *Salmonella typhimurium* (Sequence Id. 8)

| 104 A | F | L | L | A | — | V | I | — | I | G | V | S | A | G | V | I | A | A | L K Q N T R 126 |
|---|---|---|---|---|---|---|---|---|---|---|---|---|---|---|---|---|---|---|---|
| * | * | * | * | | | * | | | : | * | * | | : | | | | | | : |

Galactose permease: *Saccharomyces cerevisiae* (Sequence Id. 9)

| 486 A | F | F | T | P | — | F | I | — | T | S | A | I | N | F | Y | Y | G | Y | V F M G C L 508 |
|---|---|---|---|---|---|---|---|---|---|---|---|---|---|---|---|---|---|---|---|
| * | * | : | : | | | : | : | | * | : | * | * | | | : | | | | |

Quinate permease: *Aspergillus nidulans* (Sequence Id. 10)

| 458 F | F | F | A | S | — | L | M | — | I | L | S | I | V | F | V | F | F | L | I P E T K G 480 |
|---|---|---|---|---|---|---|---|---|---|---|---|---|---|---|---|---|---|---|---|
| * | : | : | | | | * | | | | * | * | | : | : | * | | * | : | * * * |

Phosphoglycerate transporter: *S. typhimurium* (Sequence Id. 11)

| 366 Q | F | L | A | S | — | V | Q | — | T | M | E | I | V | P | S | F | A | V | G S A V G L 388 |
|---|---|---|---|---|---|---|---|---|---|---|---|---|---|---|---|---|---|---|---|
| * | * | * | : | * | | : | | | : | | : | | | * | : | | * | : | * |

Gastric H+K+-ATPase alpha subunit: human (Sequence Id. 12)

| 254 A | F | F | S | T | — | M | C | — | L | E | G | T | A | Q | G | L | V | V | N T G D R T 276 |
|---|---|---|---|---|---|---|---|---|---|---|---|---|---|---|---|---|---|---|---|
| * | | * | | * | | * | | | : | | * | * | | | : | * | * | : | * : * : |

TABLE 2-continued

Sequence homology between *H. pylori* vacuolating toxin and ion channel or transport proteins Sequence Start                                                                                                                                        Finish Ca++-ATPase from sarcoplasmic reticulum: rabbit (Sequence Id. 13)

208 L   F   S   G   T   —   N   I   —   A   A   G   K   A   L   G   I   V   A   T   T   G   V   S   T 230
                                  *           *   *           :   :   :   *   *                   :           :   :

Chromaffin granule H+-ATPase 16 kDa proteolipid subunit: bovine (Sequence Id. 14)

50 E   M   I   M   K   —   S   I   —   I   P   V   V   M   A   G   I   I   A   I   Y   G   L   V   V 72
   *   *       :   :       *   *       *                       *           *   *               :

*indicates identity with *H. pylori* Mr = 87,000 protein subunit: indicates conservative substitutions Determination of the molecular mass of the non-denatured toxin (CB antigen) was performed on a SUPEROSE 6 HR 10/30 column (Pharmacia) with buffer containing 60 mM Tris-HCl and 0.1M NaCl (pH 7.7). Standards (Sigma, St. Louis, Mo.) included salmon sperm DNA (void volume), blue dextran (2,000,000), bovine thyroglobulin (669,000), horse spleen apoferritin (443,000), beta-amylase from sweet potato (200,000), bovine serum albumin (66,000), and carbonic anhydrase from bovine erythrocytes (29,000). The toxin preparation used in this analysis was partially purified by hydrophobic interactive and gel filtration chromatography, and then applied to the SUPEROSE (Pharmacia) 6 HR 10/30 column. Vacuolating toxin activity, as detected in cell culture, as well as the Mr=87,000 band detected by SDS-PAGE, were present in several fractions, each with an Mr greater than 972,000, suggesting aggregation. To determine whether aggregation resulted from processes used in the purification, unconcentrated broth culture supernatant from *H. pylori* 60190 was passaged through the same column, and fractions were analyzed in an ELISA for reactivity with antiserum to the Mr=87,000 protein subunit. Multiple fractions containing proteins with calculated molecular weights greater than 100,000 were recognized by the antiserum, an indication that aggregation of the Mr=87,000 protein subunit also occurred in unprocessed supernatant.

The pI of the purified toxin was determined by isoelectric focusing. Isoelectric focusing was performed on a Resolve Alpha horizontal electrophoresis unit (Isolab, Inc., Akron, Ohio) using a 5% acrylamide gel (LKB, Bromma, Sweden) containing 5M urea and 2.5% ampholytes (pH range 3.5–9.5). Standards (Sigma) were trypsin inhibitor (4.6), beta-lactoglobulin A (5.13), bovine carbonic anhydrase II (B) (5.9), and human carbonic anhydrase B (6.6). The purified denatured *H. pylori* Mr=87,000 protein subunit and isoelectric focusing standards were transferred to nitrocellulose paper by electroblotting for one hour. The standards were resolved by staining with Coomasie blue, and the *H. pylori* protein was resolved by immunoblotting with specific antiserum, using the methods described below. The non-denatured toxin failed to migrate in a 1% agarose gel (Isolab, Akron, Ohio), presumably due to its large size, Therefore, the Mr=87,000 protein subunit was eluted from an SDS-PAGE gel fragment, and focusing in a 5% acrylamide gel containing 5M urea indicated a pI of approximately 6.1.

EXAMPLE 3

PCR Amplification of a Toxin-Encoding DNA Sequence and Cloning of Toxin Gene

In order to determine internal amino acid sequences, the CB antigen from *H. pylori* 60190 was purified by column chromatography as described by Cover et al. in Purification and Characterization of the Vacuolating Toxin from *Helicobacter pylori*, *J. Biol. Chem.* 267: 10570–575 (1992). See Example 1 for a description of the chromatography.

The purified 87 kDa band was immobilized on PVDF paper, and excised. Amido-black-stained excised protein bands were washed once with Milli-Q water and destained with 0.5 ml of 200 μM NaOH/20% acetonitrile for 1 minute, followed by one wash with Milli-Q water. The remaining nonspecific protein binding sites were blocked with 0.5 ml of 0.2% PVP-40/methanol (w/v) at room temperature for 30 minutes followed by addition of 0.5 ml of Milli-Q water. Samples were washed 6–10 times with 1 ml Milli-Q water to remove excess PVP-40, cut into approximately 1×1-mm squares, and returned to the same Eppendorf tube. Fifty microliters of 1% RTX-100/10% acetonitrile/100 mM Tris-HCL, pH 8.0, was added to the strips, followed by 5 μl of Arg-C protease. The best results were obtained with digestion buffer volume less than 50 μl. Digestion was carried out at 37° C. for 24 hours. In experiments utilizing >0.001% SDS in the digestion buffer, an extraction with heptane/isoamyl alcohol (4:1, v/v) was performed prior to HPLC analysis. Frank, R. W., and Bosserhoff, A. (1988) in *Methods in Protein Sequence Analysis* (Wittmann-Liebold, B., Ed.), pp. 273–279, Springer Verlag, Berlin Heidelberg. Following digestion, samples were sonicalted for 5 minutes and then centrifuged at 1700 rpm for 5 minutes, and the supernatant was transferred to an HPLC injection vial (Hewlett-Packard). Consecutive washes with 50 μl of digestion buffer (1×) and 50 μl 1.1% TFA (2×) were performed with sonication and centrifugation as described above. All supernatants were pooled for a total of 200 μl. If samples were not immediately analyzed by HPLC, the digestion was stopped by addition of 2 μl of 1% DFP/ethanol (v/v) to the pooled supernatants and the vial stored at −20° C.

Peptide isolation was performed on a 1090M HPLC (Hewlett-Packard, Avondale, Pa.) equipped with a binary solvent delivery system, a diode array detector, a variable-volume injector, and an autosampler. The effluent from the flowcell was directly attached to a fraction collector using capillary tubing that had a dead volume of 9 μl. Data were collected using Hewlett-Packard 79995A Chem-Station software. Peptides were injected (200 μl) and separated on a Vydac $C_{18}$ column (2.1×250 mm) with a flow rate of 150 μl/minutes at room temperature. Chromatographic conditions were as described by Stone et al. Stone, K. L., LoPresti, M. B., Williams, N. D., Crawford, J. W., DeAngelis, R., and Willaims, K. R. (1989) in *Techniques in Protein Chemistry*

(Hugli, T. E., Ed.), pp. 377–390, Academic Press, New York. Briefly, the gradient was 1.6–29.6% B (0–63 minutes), 29.6–60% B (63–95 minutes), 60–80% B (95–105 minutes), and the buffers were A=0.1% TFA/Milli-Q water and buffer B=0.08% TFA/acetonitrile. The column was then washed at 80% B for 12 minutes at 150 μl/minute and reequilibrated at 1.6% B for 50 minutes at 300 μl/minute. Peptide elution was monitored at 220 nanometers. Fractions were collected every 0.5 minutes (75 μl/fraction) and stored at −20° C. until sequence analysis was performed. Microseqencing of internal peptides was then performed as described in Fernandez (Anal. Biochem. 1992; 201:255–264).

Microsequencing of three peptides yielded the following amino acid sequences (parentheses indicate ambiguous residues);

(L) G Q F N G N (S) F T (S) Y K D X A D
SEQUENCE ID. NO. 15.
(N) I K N V E I T R
SEQUENCE ID . NO. 16.
(T)R V/I D F N A K N I L I D N F L E I N N R
SEQUENCE ID. NO. 17.

Using this information degenerate oligonucleotide primers were synthesized corresponding to amino acid residue numbers 2–8 of Sequence Id. no. 2 and amino acid residues numbers 13–20 of the internal peptide previously designated Sequence Id. no. 17.

5' T T Y T T Y A C N A C N G T N A T H A T 3'
SEQUENCE ID. NO. 18
5' G A Y A A Y T T Y Y T N G A R A T H A A Y A A 3'
(sense)
SEQUENCE ID. NO. 19
3' C T R T T R A A R R A N C T Y T A D T T R T T 5'
(antisense)
SEQUENCE ID. NO. 20

TABLE 3

| | |
|---|---|
| R = A, G | H = A, T, C, NOT G |
| Y = C, C | B = G, T, C, NOT A |
| M = A, C | V = G, A, C, NOT T |
| K = G, T | D = G, A, T , NOT C |
| S = G, C | N = G, A, T, C |

Symbols used in the degenerate primers are shown in table 3.

The degenerate oligonucleotide primers were synthesized using standard phosphoramididite chemistry on a DNA synthesizer. These degenerate oligonucleotides (Sequence Id Nos. 18 and 20) were used as primers in a polymerase chain reaction designed to amplify the intervening sequences of the toxin gene. *H. pylori* 60190 cells were harvested from blood agar plates in distilled water, boiled for five cycles at 100° C., and centrifuged to remove debris; the supernatant was used as the DNA template for PCR.

PCR was performed using a Perkin Elmer DNA thermal cycler according to the manufactures instructions. PCR was performed for five cycles using temperatures of 94° C. for 1.5 minutes, 37° C. for two minutes, and 72° C. for two minutes, followed by forty-five cycles using temperatures of 94° C. for 1.5 minutes, 41° C. for two minutes, and 72° C. for two minutes. Analysis of the amplified DNA by agarose gel electrophoresis revealed a dominant band migrating at 0.5 kb.

The 0.5 kb amplified DNA fragment was cut from the agarose gel, purified, and cloned into NOVABLUE (Novagen) cells using a pT7blue T-vector kit (Novagen). Plasmid DNA was purified from the transformant, and digestion with PstI and BamHI confirmed the presence of the 0.5 kb insert. Dideoxynucleotide sequencing of the insert using lambda ZAP vector primers was performed using standard methodology. Sanger et al., *Proc. Nat'l. Acad. Sci. USA* 71:1342–46 (1977), and Maniatis, et al., *Molecular Cloning: A Laboratory Manual Cold Spring Harbor*, N.Y., 1989. The nucleic acid sequence of the amplification product is set out in sequence Id. no. 1 ( in the 5' to 3' direction bases 24–495). Portions of this sequence correctly encoded the amino acid sequences Id. Nos. 2, 15, and 17, indicating that a portion of the toxin gene had been successfully cloned. Specifically, sequence Id. No. 15 was encoded by bases 400–450 of sequence Id. No. 1.

To clone the entire toxin gene, chromosomal DNA from *H. pylori* 60190 was sheared by sonication and the resulting fragments electrophoresed on a 0.7% agarose gel. Fragments in the 2–10 kb size range were excised, treated with T4 DNA polymerase to produce blunt ends, and ligated to phosphorylated EcoRI octamer linkers (New England Biolabs). The DNA was digested EcoRI and ligated to the EcoRI arms of lambdaZAP vector (Stratagene). The ligation mixtures were added to Gigapack II packaging mix (Stratagene) and titered on XL1-blue cells. The cloned 0.5 kb fragment of the toxin gene described above was radiolabelled by primer extension using random hexamers, and used to screen the genomic library. From eight reactive clones, the recombinant phagemids were excised and transformed into XL1-blue cells. Plasmid DNA from these clones revealed DNA inserts of 1.2, 1.1, or 2.2 kb. Three representative clones containing these insert sized were used in further studies (p1A1, p3A1, and p3C), respectively. Restriction endonuclease treatment of these recombinant plasmids revealed no overlap between p1A1 and p3A1.

Partial sequences of p1A1 and p3A1 were determined using both forward and reverse vector primers. DNA sequence corresponding to the N-terminal amino acid sequence of the toxin was identified in p3A1, and sequences corresponding to internal amino acid sequence set out in sequence Id. nos. 15 and 17 were identified in p1A1. The 1.1 kb insert in p3A1 contained sequence corresponding to bases 1–177 of sequence Id. No. 1, as well as approximately 0.9 kb of an upstream sequence. The 1.2 kb insert in p1A1 contained sequence corresponding to bases 178–1412 of the sequence set out in sequence Id. no. 1.

Expression of Recombinant Toxin in *E. Coli*

Clone 3A1 contained 177 bases of the toxin gene (including the N-terminal amino sequence), a leader sequence, probable promoter, and approximately 0.8 Kb of upstream sequence. Clone 1A1 contains 1.2 kb of internal toxin gene (sequences 177–1412), and flanks the EcoR1 site which is at the downstream end of 3A1. One approach to express the toxin recombinantly is to PCR amplify the 1412 basepair fragment of the toxin gene, using as primers bases 1–20 and bases 1392–1412 of sequence Id no. 1. This sequence can then be subcloned into pBluescript in *E. coli* XL1Blue, and the recombinant toxin can be expressed. Alternatively, the DNA inserts in 3A1 and 1A1 can be excised from the pBlusescript plasmid and gel purified. Insert 3A1 can be cut at an internal restriction site, and the fragments of 3A1 gel-purified. The fragment of 3A1 containing the desired portion of the toxin gene (promoter, leader sequence, and bases 1–177) can be ligated to insert 1A1 and subcloned into pBluescript. In both of these cases, production of recombinant toxin by pBluescript may be inducible by IPTG. If recombinant toxin is not expressed in pBluesript, alternate expression vectors involving production of fusion proteins, such as pGEX2T, can be used.

As discussed in this example, approximately 55% of the toxin gene has been cloned and sequenced; however, using a downstream portion of the known sequence as a probe, the lambda ZAP II library can be rescreened, in order to clone and sequence the remainder of the toxin gene. Construction of a sequence encoding the entire gene can then be performed using methods similar to those discussed above, and the entire recombinant toxin can then be expressed in *E. coli.*

EXAMPLE 4

Detection of *H. Pylori* Toxin Gene by Polymerase Chain Reaction or Probe Hybridization Diagnostic tests for *H. pylori* infection can be developed based on primer directed amplification of samples. More specifically, synthetic oligonucleotides selected from the nucleotides set out in sequence Id. no. 1 can be used in a polymerase chain reaction to amplify *H. pylori* toxin to detectable levels. In this test nondegenerate primer sequences are used for PCR. These nondegenerate primer sequences are selected from the nucleic acids set out in sequence Id. no. 1. More specifically, they may include:

5' TTTTTTACAACCGTGATCAT 3' Sequence Id. no 21.

3' CTATTAAAAAATCTTTAGTTATT 5' Sequence Id. no. 22.

With the use of these primers, a 0.5 kb amplification product is produced, as indicated in Example 3. Alternatively, the toxin gene may be detected by hybridization of clinical samples with the radiolabelled sequence ID Number 1, or a portion 15 thereof.

EXAMPLE 5

Use of specific antiserum to the toxin in detection and neutralization of the CB antigen.

Antiserum to the Mr=87,000 protein subunit was raised in a female White New Zealand rabbit, according to the regimen described previously (Cover, T. L., Dooley, C. P., and Blaser, M. J. (1990) *Infect. Immun.* 58:603–610). Initially, the rabbit was immunized with Coomasie blue-stained acrylamide gel fragments containing the denatured Mr=87,000 protein subunit. Subsequently, the rabbit was immunized with the denatured Mr=87,000 protein subunit that was eluted in distilled water from unstained SDS-PAGE gels, and concentrated by hydrophobic interactive chromatography as described above.

Preimmune and immune serum were assessed by Western blot analysis. Following separation by SDS-PAGE, proteins in *H. pylori* culture supernatant were transferred to nitrocellulose paper by electroblotting for one hour at one amp. Nitrocellulose paper strips were incubated with sera, washed, incubated with alkaline phosphatase-conjugated anti-human IgG (Boehringer-Mannheim, Indianapolis, Ind.) or anti-rabbit IgG (Tago, Burlingame, Calif.), and developed as described by Blake et al. (Blake, M. S., Johnston, K. H., Russel-Jones, G. I., and Gotschlich., E. C. (1984) *Anal. Biochem.* 136:175–179). Antiserum raised against the purified Mr=87,000 protein subunit recognized the Mr=87,000 protein band and no other *H. pylori* constituents (FIG. 3).

Preimmune and immune rabbit sera were also assessed by ELISA. The ELISA was performed with 15 ng purified CB antigen per microtiter well, and the methodology was as previously described (Perez-Perez, G. I., Dworkin, B. M., Chodos, J. E., and Blaser, M. J. (1988) *Ann. Intern. Med.* 109:465–471 hereby incorporated by reference). Peroxidase-conjugated anti-human IgG (Tago) or anti-rabbit IgG (Boehringer Mannheim) were used as the conjugates. The titer of rabbit serum was defined as the reciprocal of the highest dilution that produced an optical density of greater than 0.2. Using this methodology, the titer of the antiserum was 1:512,000, whereas that of the preimmune serum was <1:200.

Neutralization of vacuolating toxic activity. The toxin preparation used in neutralization assays was prepared by culturing *H. pylori* 60190 for 48 hours in Brucella broth containing 5% fetal bovine serum, centrifuging the culture, and concentrating the supernatant by ultrafiltration, as previously described (Cover, T. L., Purycar, W., Perez-Perez, G. I., and Blaser, M. J. (1991) *Infect. Immun.* 59:1264–1270). Sera were heated at 56° C. for 30 minutes, diluted in tissue culture medium, and incubated for one hour with an equal volume of concentrated *H. pylori* supernatant, as previously described (Cover, T. L., Cao, P., Murthy U. K., Sipple, M. S., and Blaser, M. J. (1992) *J. Clin. Invest.* 90:913–918.) The neutralizing effects of sera on the vacuolating toxic activity were quantitated using the neutral red uptake assay (Cover, T. L., Puryear, W., Perez-Perez, G. I., and Blaser, M. J. (1991) *Infect. Immun.* 59:1264–1270). Under the assay conditions used, at a 1:64 dilution the antiserum completely neutralized vacuolating toxin activity in supernatant from *H. pylori* 60190, whereas preimmune serum lacked neutralizing activity (FIG. 4). The antiserum also completely neutralized the toxin activity present in culture supernatants from two other toxin-producing *H. pylori* strains, an indication that the vacuolating toxins produced by various *H. pylori* isolates are antigenically related.

TABLE 4

*H. pylori* isolates from humans used in the study

| Strain | Source | Toxin production | Reciprocal toxin titer[a] |
|---|---|---|---|
| 60190 | ATCC 49503 | + | 320 |
| 85-456 | NTCC 11638 | + | 40 |
| 87-29 | Colorado | + | 160 |
| 87-199 | Colorado | + | 80 |
| 87-81 | Colorado | + | 40 |
| 87-90 | Colorado | + | 40 |
| 86-86 | New York | + | 80 |
| 88-43 | Thailand | + | 20 |
| Tx30a | Texas | − | <10 |
| 87-141 | Colorado | − | <10 |
| 87-75 | Colorado | − | <10 |
| 86-385 | Colorado | − | <10 |
| 86-313 | Colorado | − | <10 |
| 87-6 | Colorado | − | <10 |
| 87-225 | Colorado | − | <10 |
| 87-203 | Colorado | − | <10 |

[a]The reciprocal toxin titer was defined as the greatest dilution that induced HeLa cell neutral red uptake greater than 3 SD above that induced by medium alone, as described (Cover, T.L., Puryear, W., Perez-Perez, G.I., and Blaser, M.J. (1991) Infect. Immun. 59:1264–1270).

Detection of the vacuolating toxin in *H. pylori* culture supernatants.

The next experiment was designed to determine whether there was a relationship between vacuolating toxin activity and presence of the CB antigen in *H. pylori* culture supernatants. From a collection of concentrated *H. pylori* culture supernatants, we selected supernatants from 8 $tox^+$ and 8 $tox^-$ strains (Cover, T. L., Dooley, C. P., and Blaser, M. J. (1990) *Infect. Immun.* 58:603–610).

These *H. pylori* strains (Table 4) were cultured in Brucella broth containing 5% fetal bovine serum, and the culture supernatants were concentrated by ultrafiltration as previously described (Cover, T. L., Dooley, C. P., and Blaser, M. J. (1990) *Infect. Immun.* 58:603–610).

To quantitate vacuolating toxin activity, dilutions of each of these supernatants were tested using the neutral red assay (Cover, T. L., Puryear, W., Perez-Perez, G. I., and Blaser, M. J. (1991) Infect. Immun. 59:1264–1270). Diluted greater than 1:20, each of the tox$^+$ supernatants induced greater than two-fold greater net neutral red uptake by cells than medium alone, whereas each of the tox$^-$ supernatants failed to induce significant neutral red uptake when diluted 1:10. To detect the CB antigen, the 16 supernatants were tested by ELISA with a 1:10,000 dilution of antiserum to the Mr=87,000 protein subunit (FIG. 5). The supernatants from tox$^+$ strains produced significantly higher optical density values than supernatants from tox$^-$ supernatants (0.614±0.105 versus 0.046±0.009, p <0.0001). Western blotting studies confirmed the presence of the Mr=87,000 band in each of the tox$^+$ supernatants, indicating that this is the form of CB antigen under denatured conditions. The lack of overlap between these two groups of supernatants indicates that the CB antigen is the major substituent in H. pylori supernatants that mediates vacuolating toxin activity.

EXAMPLE 6

Detection of anti-toxin antibodies in body fluids from H. pylori-infected humans Previous studies have demonstrated that sera from some, but not all H. pylori-infected persons contain toxin-neutralizing antibodies (Leunk, R. D., Ferguson, M. A., Morgan, D. R., Low, D. E., and Simor, A. E. (1990) J. Clin. Microbiol. 28:1181–1184; Cover, T. L., Cao, P., Murthy U. K., Sipple, M. S., and Blaser, M. J. (1992) J. Clin. Invest. 90:913–918.) We therefore sought to determine the prevalence of antibodies to the purified CB antigen protein in sera from H. pylori-infected and uninfected humans.

Human sera were obtained from forty selected symptomatic patients who had previously undergone gastroduodenal endoscopy at the University Hospital and the Veterans Administration Medical Center, Syracuse, N.Y. Based on analysis of the gastric biopsy specimens and serologic evaluation of these patients, 20 were infected with H. pylori and twenty were uninfected. The characteristics of these patients and the toxin-neutralizing activities of these sera have been previously described (Cover, T. L., Cao, P., Murthy U. K., Sipple, M. S., and Blaser, M. J. (1992) J. Clin. Invest. 90:913–918.) These 40 sera were tested for IgG reactivity with the purified CB antigen in an ELISA (FIG. 6).

The ELISA was performed with 15 ng purified CB antigen per microtiter well, and the methodology was as previously described (Perez—Perez, G. I., Dworkin, B. M., Chodos, J. E., and Blaser, M. J. (1988) Ann. Intern. Med. 109:465–471 hereby incorporated by reference). Peroxidase-conjugated anti-human IgG (Tago) or anti-rabbit IgG (Boehringer Mannheim) were used as the conjugates. The mean recognition of the CB antigen by sera from H. pylori-infected persons was significantly stronger than by sera from uninfected persons (p=0.0009). Sera from approximately half of the H. pylori-infected persons produced optical density values that overlapped those of uninfected persons, whereas sera from other H. pylori-infected persons produced optical density values that did not overlap. This suggests that two populations may be present, and is consistent with the observation that 50%–60% of H. pylori strains are toxigenic in vitro. We then determined whether there was a relationship between recognition of the CB antigen by ELISA and toxin-neutralizing activity, as determined previously in the cell culture assay (Cover, T. L., Cao, P., Murthy U. K., Sipple, M. S., and Blaser, M. J. (1992) J. Clin. Invest. 90:913–918.) For sera from H. pylori-infected persons, ELISA recognition of the CB antigen was significantly associated with toxin-neutralizing activity (p=0.019, r=0.518 by linear regression analysis). In contrast, for sera from uninfected persons, these variables were not significantly associated (p=0.973, r=0.008).

EXAMPLE 7

Preparation of an oral vaccine for administration to mammals including humans

We have considered the potential application of the use of the CB protein in the development of a vaccine against H. pylori infections. To limit the effects of gastric acid and proteolytic enzymes on the vaccine preparation, the whole CB protein or a portion thereof can be packaged either in an enteric coated gelatin capsule or administered with sodium bicarbonate (Black et al, "Immunogenicity of Ty21a attenuated Salmonella typhi given with sodium bicarbonate or in enteric-coatzed capsules." Dev. Biol. Stand. 53:0, 1983). It should be noted that the antigen used in this vaccine could be produced recombinantly. Dosage for adult humans preferably varies from 5.0–50.0 mg of the antigens of the invention.

To enhance delivery of CB protein to the gastrointestinal immune system the protein [or a fragment(s) of the protein] may be incorporated without chemical coupling into biodegradable microspheres that are 5–10 230 μm in size that will be ingested orally (Eldridge et eil., "Biodegradable microsphere: vaccine delivery systems for oral immunization," Curr. Top. Microbiol. Immunol. 146:59, 1989). The microspheres are composed of co-polymers of glycolic and lactic acids which are degraded into original components by hydrolysis. Adjusting the ratio of glycolic to lactic acids within the co-polymers varies the rate of hydrolysis from several hours to several months. Thus, both fast- and slow-releasing microspheres can be created. The use of a mixture of both fast- and slow-releasing microspheres will then be used to allow for induction of both a primary and secondary immune response with a single oral immunization.

EXAMPLE 8

Preparation of a parenteral vaccine for administration to mammals including humans Although for gastrointestinal pathogens, orally administered vaccines appear to be preferable, for several other infectious agents, parenteral vaccine show efficacy. A component of the bacterium Salmonella typhi, the cause of typhoid fever, has been purified and used as a parenteral-administered vaccine. This component, the Vi capsular polysaccharide, is highly efficacious (Klugman KP, et al., "Protective activity of Vi capsular polysaccharide vaccine against typhoid fever," Lancet 1987;2:165–69"). The Salk vaccine for polio is administered parenterally and it prevents the disease of polio, although having little or no effect on becoming infected with the polioviruses. Parenteral vaccines also have efficacy, although limited, in preventing cholera.

For H. pylori, a parenteral vaccine could include CB protein or fragments thereof. A toxoid preparation could also be prepared, analogous to the use of diphtheria or tetanus toxoids. The protein(s) or fragment(s) could be administered with an adjuvant or by itself in a suitable buffer. Adjuvants include, but are not limited to, muramyl dipeptide, concanavalin A, DEAE dextran, lipid polyvalent cations, or hydrocarbons such as hexadecane.

H. pylori vaccine could be given to humans as 1.0 mg (range 0.5–5.0 mg) of antigen (CB protein) in 1 ml of phosphate buffered saline (pH 7.4). With a suitable antigen, only a single dose may be needed, but multiple doses with or without adjuvants could be considered.

EXAMPLE 9

Test kits for detection of antibodies to H. pylori toxin, and for detection of H. pylori toxin Specific test kits are constructed for detecting antibodies using several different techniques for detection. One test kit for antibody detection is comprised of a compartmented enclosure containing a plurality of wells, plates which were coated prior to use with CB protein or an antigenic fragment thereof, and ELISA materials for enzyme detection consisting of peroxidase-labeled goat anti-human IgG and a color change indicator consisting of ABTS in McIlvain's buffer with 0.005 percent hydrogen peroxide. It should be noted that the antigen used in an assay could made recombinantly. Naturally, other enzymes and developers could have been used. For instance, alkaline phosphatase-labeled goat anti-human IgG could be used in conjunction with p-nitrophenyl phosphate in diethanolamine and magnesium chloride buffer.

A second test kit for detecting antibodies using the Western blot technique is comprised of a container, cover, nitrocellulose sheet, and a polyacrylamide slab gel in the presence of sodium dodecyl sulfate, surfactants, pH modifiers, dried nonfat milk and materials for enzyme detection including a color change indicator consisting of DAB in Tris with hydrogen peroxide. This Western blot analysis kit also contains peroxidase-labeled goat or rabbit anti-human immunoglobulin and a source of CB protein or antigenic fragment thereof.

Another H. pylori specific test kit for detecting antibodies using the indirect immunofluorescence assay may include a compartmental container with CB protein or antigenic fragments thereof as antigens, human test serum, phosphate buffered saline and fluorescein-conjugated goat anti-human IgG.

Finally, a different H. pylori specific test kit for detecting antibodies uses liposomes and comprises a container, human test serum, fluorescent marker- (or enzyme- or substrate-) filled liposomes with antigens on their surface, and a surface-active agent. In this assay the container might be a precoated tube or well with goat anti-human IgG.

H. pylori specific test kits are constructed for detecting H. pylori toxin using several different techniques for detection. One test kit for detection of H. pylori toxin comprises a compartmented enclosure containing a plurality of wells, plates that could be coated with the sample to be tested, a hyperimmune antiserum (or monoclonal antibodies) to CB protein or antigenic fragment thereof, anti-rabbit immunoglobulin and appropriate ELISA materials such as those discussed above in this example.

A second test kit for detecting H. pylori toxin using the Western blot technique is comprised of a container, cover, nitrocellulose sheet, and a polyacrylamide slab gel in the presence of sodium dodecyl sulfate, surfactants, pH modifiers, dried nonfat milk and materials for enzyme detection including a color change indicator consisting of DAB in Tris with hydrogen peroxide. This Western blot analysis kit also contains goat anti-rabbit immunoglobulin and a source of hyperimmune antiserum to CB protein or antigenic fragment thereof.

Another H. pylori specific test kit for detecting the toxin using the latex agglutination assay may include a compartmental container, hyperimmune serum to CB protein or antigenic fragment thereof conjugated to latex beads, and phosphate buffered saline or water.

EXAMPLE 10

Inhibition of H. pylori vacuolating toxin activity by bafilomycin A1.

The cellular vacuoles that form in response to H. pylori vacuolating toxin are acidic in pH. (Cover T L, Halter S A, M J Blaser. 1992. "Characterization of HeLa cell vacuoles induced by H. pylori broth culture supernatant." *Human Pathology* 23:1004–1010). The maintenance of pH gradients within compartments of eukaryotic cells typically is dependent upon the activity of a vacuolar-type proton-transporting ATPase (Mellman I, Fuchs R, and A Helenius. 1986. "Acidification of the endocytic and exocytic pathways." *Annu. Rev. Biochem.* 55:663–700). We hypothesized that the vacuolar ATPase of eukaryotic cells might be important in the formation and maintenance of H. pylori toxin-induced vacuoles. Therefore, we tested the effects of vacuolar ATPase inhibitors upon H. pylori toxin-induced cell vacuolation.

HeLa cells were incubated with H. pylori toxin in the presence of nine different inhibitors of ion-transporting ATPases (bafilomycin A1, N-ethylmaleimide (NEM), 7-chlor-4-nitrobenz2-oxa-1,3-diazole (NBD chloride), N,N'dicyclohexylcarbodiimide pentachlorophenol complex (DCCD), sodium nitrate, ouabain, digoxin, sodium orthovanadate, omeprazole, and oligomycin).

More specifically, H. pylori 60190, a well characterized strain that produces the vacuolating toxin, was cultured for 48 hours at 37° C. in Brucella broth supplemented with 5% fetal bovine serum in a 5% $CO_2$ atmosphere. After centrifugation of the culture, supernatant was concentrated 30-fold by ultrafiltration and passed through a 0.2 micron filter. Supernatants were stored at −70.0° C. prior to testing in tissue culture assays. Purified toxin was prepared from H. pylori 60190 as previoulsy described except that gel filtration chromatography was performed with a SUPEROSE 6 HR 10/50 column (Pharmacia) instead of SUPEROSE 12HR 10/50 column (Pharmacia).

HeLa cells were cultured in Eagle's modified minimal essential medium with Earle's salts containing 10% fetal bovine serum and 25 mM HEPES buffer (pH 7.2) in a 5% $CO_2$ atmosphere. In experiments involving purified H. pylori toxin, the medium was supplemented with 10 mM ammonium chloride to potentiate activity. After preincubation of the cells with ATPase inhibitors for one hour, concentrated culture supernatant or purified toxin from H. pylori 60190 was added and cells were incubated for an additional eighteen hours at 37° C. Vaculation was assessed visually by inverted light microscopy (200× magnification), or quantitated using a neutral red uptake assay. (Cover et al., Infect. Immun, 59:1264–1270 (1991)). In a microscopic assay, inhibition of *H. pylori* vacucolating toxin activity was defined by the stringent criterion of visible vacuoles in less the ten percent of the cells.

Inhibitors of predominantly vacuolar-type ATPases inhibited the formation of vacuoles in response to the *H. pylori* toxin, and reversed the vacuolation induced by the toxin. Of the vacuolar ATPase inhibitors tested, bafilomycin A1 was the most potent inhibitor of toxin-induced vacuolation (minimum inhibitory concentration=25 nM). Vacuolating toxin activity was inhibited by higher concentrations of other vacuolar ATPase inhibitors, including N-ethylmaleimide, 7-chloro-4-nitrobenz-2-oxa-1,3-diazole, N,N'-dicyclohexylcarbodiimide, and sodium nitrate. In contrast, $F_1F_0$-type or P-type ATPase inhibitors did not inhibit toxin activity. (See table 5.)

TABLE 5

Inhibition of *H. pylori* toxin-induced vacuolation by ATPase inhibitors

| Inhibitor | Minimum inhibitory concentration (MIC) for *H. pylori* toxin[a] | Predominant class of ATPase inhibited | $IC_{50}$ for eukaryotic vacuolar ATPase[b] |
|---|---|---|---|
| Bafilomycin | 25 nM | V-type | 2–10 nM |
| N-ethylmaleimide (NEM) | 25 uM | V-type | 1–13 uM |
| NBD-Cl[c] | 50 uM | V-type | 2.5 uM |
| DCCD[d] | 25 uM | V-type, $F_1F_0$ | 5–20 uM |
| Sodium nitrate | 100 mM | V-type | 30–100 mM |
| Ouabain | >100 uM | P-type | >2000 uM |
| Vanadate | >100 uM | P-type | >100 uM |
| Omeprazole | 200 uM | Gastric | ≧100 uM |
| Oligomycin | >50 uM | $F_1F_0$ | 50 uM |

[a]The minimum concentration required to inhibit vacuole formation in >90% of HeLa cells incubated with a 1:10 dilution of concentrated supernatant from *H. pylori* strain 60190; result shown is median of three experiments.
[b]The concentration of agent required for half-maximal inhibition of vacuolar proton transport in cell-free systems.
[c]7-chloro-4-nitrobenz-2-oxa-1,3-diazole
[d]N,N'-dicyclohexylcarbodiimide In summary, inhibitors of vacuolar-type ATPase, exemplified by bafilomycin A1, are inhibitors of cellular damage induced by *H. pylori* vacuolating toxin, and may be useful therapeutic agents in the treatment of *H. pylori*-associated gastroduodenal disease.

Although the invention has been described primarily in connection with special and preferred embodiments, it will be understood that it is capable of modification without departing from the scope of the invention. The following claims are intended to cover all variations, uses, or adaptations of the invention, following, in general, the principles thereof and including such departures from the present disclosure as come within known or customary practice in the field to which the invention pertains, or as are obvious to persons skilled in the field.

We claim:

1. An isolated nucleic acid encoding an *H. pylori* vacuolating toxin, or a nucleic acid fragment consisting of at least 20 nucleotides from an *H. pylori* vacuolating toxin-encoding nucleic acid.

2. An isolated nucleic acid encoding an *H. pylori* vacuolating toxin comprising the nucleic acid set forth in the Sequence Listing as SEQ ID NO:1.

3. An isolated nucleic acid consisting of the nucleotides set forth in the Sequence Listing as SEQ ID NO:1.

4. An isolated oligonucleotide consisting of the nucleotides set forth in the Sequence Listing as SEQ ID NO:21.

5. An isolated oligonucleotide consisting of the nucleotides set forth in the Sequence Listing as SEQ ID NO:22.

6. A diagnostic test kit for detecting *H. pylori* toxin nucleic acids in a sample, said test kit comprising:

(a) two single stranded oligonucleotides of at least 20 nucleotides consisting of nucleic acid fragments specific for the nucleic acid set out in sequence Id. no 1;

(b) means for conducting PCR reaction; and (c) means for detecting *H. pylori* toxin nucleic acids.

7. A method of detecting *H. pylori* vacuolating toxin nucleic acids in a sample from a human subject by primer directed amplification wherein said sample is amplified with dual primers consisting of two single stranded oligonucleotides comprising oligonucleotides of the nucleic acid of claim 1, specific for an *H. pylori* vacuolating toxin-encoding nucleic acid, the fragment having at least 20 nucleotides, to generate an amplification product, and following said amplification hybridizing a single strand oligonucleotide probe to said amplification product and detecting said hybridized probe.

* * * * *